(12) United States Patent
Ihm et al.

(10) Patent No.: US 11,577,963 B2
(45) Date of Patent: Feb. 14, 2023

(54) METHOD OF PREPARING SPARSELY PILLARED ORGANIC-INORGANIC HYBRID COMPOUND

(71) Applicant: Innonep Inc., Seoul (KR)

(72) Inventors: Jisoon Ihm, Seoul (KR); Seok Hwan Park, Pohang-si (KR)

(73) Assignee: Innonep Inc., Seoul (KR)

( * ) Notice: Subject to any disclaimer, the term of this patent is extended or adjusted under 35 U.S.C. 154(b) by 293 days.

(21) Appl. No.: 16/911,502

(22) Filed: Jun. 25, 2020

(65) Prior Publication Data

US 2021/0221699 A1   Jul. 22, 2021

(30) Foreign Application Priority Data

Jan. 17, 2020 (KR) .................. 10-2020-0006756
Feb. 4, 2020 (KR) .................. 10-2020-0013316

(51) Int. Cl.
  *C01F 7/02* (2022.01)
  *C01F 7/021* (2022.01)
  *C07C 63/26* (2006.01)

(52) U.S. Cl.
  CPC .............. *C01F 7/021* (2013.01); *C07C 63/26* (2013.01); *C01P 2002/72* (2013.01);
  (Continued)

(58) Field of Classification Search
  CPC ...... C01G 49/009; C01G 53/006; C01G 1/00; C01G 3/006; C01G 31/006; C01G 37/006; C01G 39/006; C01G 41/006; C01G 45/006; C01G 9/006; C01P 2002/22; C01P 2002/72; C01P 2002/74; C01P 2002/78; C01P 2006/12; C01P 2006/80; C01P 2002/02; C01P 2002/77; C01P 2004/50; C01P 2004/61; C01P 2004/62;
  (Continued)

(56) References Cited

U.S. PATENT DOCUMENTS

| 4,392,979 A * | 7/1983 | Lee ........................... C01F 7/78 |
| | | 210/683 |
| 5,075,089 A | 12/1991 | Misra et al. |
| 5,578,286 A | 11/1996 | Martin et al. |

FOREIGN PATENT DOCUMENTS

| KR | 10-2008-0077638 A | 8/2008 |
| WO | WO01/12543 | 2/2001 |

(Continued)

OTHER PUBLICATIONS

Extended European Search Report for European Application No. 20182474.5, dated Dec. 7, 2020.
(Continued)

*Primary Examiner* — Victoria H Lynch
(74) *Attorney, Agent, or Firm* — Klarquist Sparkman, LLP

(57) ABSTRACT

Provided is a method of preparing a sparsely pillared organic-inorganic hybrid compound. The method of preparing an organic-inorganic hybrid compound includes: preparing a compound having a gibbsite structure by a method other than a hydrothermal synthesis method, using a trivalent metal cation source, an alkali imparting agent, and a first solvent (S10); and preparing an organic-inorganic hybrid compound by a method other than a hydrothermal synthesis method, using the compound of the gibbsite structure, a divalent metal cation source, dicarboxylic acid, and a second solvent (S20).

9 Claims, 29 Drawing Sheets

(52) U.S. Cl.
CPC ...... *C01P 2006/10* (2013.01); *C01P 2006/12* (2013.01); *C01P 2006/14* (2013.01)

(58) Field of Classification Search
CPC .............. C01P 2004/64; C01P 2006/16; C01P 2006/82; B01J 23/007; B01J 29/049; B82Y 30/00; C01B 13/145; C01B 13/363; C01B 19/002; C01B 33/38; C01F 7/00; C01F 7/78; C01F 7/785; C07C 51/412; C07C 53/126; C07C 55/10; C07C 82/08; C07C 63/28
See application file for complete search history.

(56) References Cited

FOREIGN PATENT DOCUMENTS

| WO | WO 2007/065877 A1 | 6/2007 |
|---|---|---|
| WO | WO2008/050927 | 5/2008 |

OTHER PUBLICATIONS

Extended European Search Report for European Application No. 20182479.4, dated Dec. 9, 2020.

Cesteros et al., "A New Route to the Synthesis of Fine-Grain Gibbsite", *Chem. Mater*. (2001), 13, pp. 2595-2600.

Nangoi et al., "Direct comparison among the formation of terephthalate- and carbonate-intercalated Mg—Al-LDH: The influence of the high aluminum content", *Applied Clay Science* (2018), 151, pp. 194-200.

Office Action, dated Apr. 26, 2021, issued in Korean Application No. 10-2020-0006756, 4 pages.

Office Action, dated May 17, 2021, issued in Korean Application No. 10-2020-0013315, 4 pages.

Office Action, dated May 17, 2021, issued in Korean Application No. 10-2020-0013316, 4 pages.

Besserguenev et al., Synthesis and Structure of the Gibbsite Intercalation Compounds [LiAl$_2$(OH)$_6$]X {X=Cl, Br, NO$_3$} and [LiAl$_2$(OH)$_6$]Cl•H$_2$O Using Synchrotron X-ray and Neutron Powder Diffraction, *Chem Mater*, 9:241-247 (Jan. 1997).

Nédez et al., Optimization of the Textural Characteristics of an Alumina to Capture Contaminants in Natural Gas, *Langmuir*, 12:3927-3931 (Aug. 1996).

Pérez-Bernal et al., "Nickel-aluminum layered double hydroxides prepared via inverse micelles formation," *J. Solid State Chem.*, 182(6):1593-1601 (Jun. 2009).

Rees et al., "New layered double hydroxides by prepared by the intercalation of gibbsite," *J. Solid State Chem.*, 224:36-39 (Apr. 2015).

Wikipedia, Activated carbon, https://en.wikipedia.org/wiki/Activated_carbon, 19 pages (printed Jun. 24, 2020).

\* cited by examiner

US 11,577,963 B2

METHOD OF PREPARING SPARSELY PILLARED ORGANIC-INORGANIC HYBRID COMPOUND

CROSS-REFERENCE TO RELATED APPLICATION

This application claims the benefits of Korean Patent Application Nos. 10-2020-0006756, filed on Jan. 17, 2020, and 10-2020-0013316, filed on Feb. 4, 2020, in the Korean Intellectual Property Office, the disclosures of which are incorporated herein in their entirety by reference.

BACKGROUND

1. Field

The present disclosure relates to a method of preparing a sparsely pillared organic-inorganic hybrid compound. More specifically, the present disclosure relates to a method of preparing a sparsely pillared organic-inorganic hybrid compound of which the pillar density is extremely low and the structural stability is high due to the intercalation of dicarboxylate ions in the form of pillars between inorganic material layers which are arranged in a layered structure.

2. Description of the Related Art

There have been experiments in intercalating various organic materials into gibbsite ($\gamma$-Al(OH)$_3$) or other layered-structure materials (for example, hydrotalcite) (see prior art documents 1 and 2). However, when an organic material is intercalated between layers, in general, the space between the layers may be filled up with the intercalated material, leaving few voids. Therefore, in the case of existing organic-inorganic hybrid compounds, there was little room to effectively use the interlayer space for adsorbing of other materials or collecting gas molecules.

In the related art, in factories and homes, activated carbon, aluminum oxide powder, or the like has been used as a material used for adsorbing harmful materials or storing various gases (see prior art documents 3 and 4).

Activated carbon has a high specific surface area and a well-developed micro pore structure. Thus, activated carbon is widely used to remove odors and harmful gases such as odors and to purify water. However, the pore size of activated carbon is very small and thus the total pore volume is small, the materials that can be adsorbed are limited, and the gas adsorption efficiency is rapidly reduced in high-humidity conditions (prior art document 4).

In the case of aluminum oxide, the property of adsorbing harmful materials on the surface thereof in powder form is excellent. However, aluminum oxide (or hydrotalcite-structured material which is similar thereto) has a relatively small specific surface area adsorbed and a relatively small total pore volume which limit the adsorption capacity for other materials (see prior art documents 4 and 5).

PRIOR ART DOCUMENTS

Non-Patent Documents (Non-patent document 1) A. V. Besserguenev et al., Chem. Mater. 1997, 9, 241-247

(Non-patent document 2) J. R. Rees et al., J. Solid State Chem. 2015, 224, 36

(Non-patent document 3) https://en.wikipedia.org/wiki/Activated_carbon (Non-patent document 4) C. Nedez et al., Langmuir 1996, 12, 3927-3931

(Non-patent document 5) M. E. Perez-Bernal et al., J. Solid State Chem. 2009, 182, 1593-1601

SUMMARY

One embodiment of the present invention provides a method of preparing a sparsely pillared organic-inorganic hybrid compound having an extremely low pillar density and excellent structural stability.

Additional aspects will be set forth in part in the description which follows and, in part, will be apparent from the description, or may be learned by practice of the presented embodiments of the disclosure.

One aspect of the invention provides a method of preparing an organic-inorganic hybrid compound, the method including:

preparing a compound having a gibbsite structure by a method other than a hydrothermal synthesis method, using a trivalent metal cation source, an alkali imparting agent, and a first solvent (S10); and preparing an organic-inorganic hybrid compound by a method other than a hydrothermal synthesis method, using the compound having the gibbsite structure, a divalent metal cation source, dicarboxylic acid, and a second solvent (S20).

The trivalent metal cation source may be a source of a trivalent metal cation including $Al^{3+}$, $Fe^{3+}$, $Cr^{3+}$, $B^{3+}$, $Ga^{3+}$, $In^{3+}$, $Y^{3+}$ or a combination thereof.

The alkali imparting agent may include NaOH, LiOH, KOH, LiBH$_4$, NaBH$_4$, KBH$_4$, LiH, NaH, LiAlH$_4$, NaAlH$_4$, KAlH$_4$, (i-Bu$_2$AlH)$_2$, LiHCO$_3$, NaHCO$_3$, KHCO$_3$, Li$_2$CO$_3$, Na$_2$CO$_3$, K$_2$CO$_3$, NH$_4$OH, or a combination thereof.

The first solvent or the second solvent may include water.

The compound of the gibbsite structure may be identified as an amorphous form from an X-ray diffraction (XRD) analysis result.

The divalent metal cation source may be a source of a divalent metal cation including $Zn^{2+}$, $Mn^{2+}$, $Co^{2+}$, $Ni^{2+}$, $Cu^{2+}$, $Mg^{2+}$, $Ca^{2+}$, $Sr^{2+}$, $Ba^{2+}$, or a combination thereof.

The dicarboxylic acid may include terephthalic acid, oxalic acid, malonic acid, succinic acid, glutaric acid, 2-methylglutaric acid, 3-methylglutaric acid, adipic acid, pimelic acid, suberic acid, azelaic acid, sebacic acid, undecanedioic acid, dodecanedioic acid, brassylic acid, tetradecanedioic acid, fumaric acid, 2,2-dimethylglutaric acid, maleic acid, acetylenedicarboxylic acid, glutaconic acid, 2-disendioic acid, traumatic acid, muconic acid, glutinic acid, citraconic acid, mesaconic acid, itaconic acid, tartronic acid, mesosalic acid, malic acid, tartaric acid, oxalacetic acid, aspartic acid, glutamic acid, diaminopimelic acid, saccharic acid, 2,6-naphthalenedicarboxylic acid, or combination thereof.

The organic-inorganic hybrid compound may have the properties of adsorbing or storing volatile organic compounds, environmentally harmful liquid materials, polycyclic aromatic hydrocarbons, exhaust gas-based environmental pollutants, greenhouse gases, radioactive materials, hazardous heavy metals, toxic chemicals, or hydrogen gas.

Process (S10) may include preparing a first metal salt solution by dissolving the trivalent metal cation source in the first solvent (S10-1), preparing an alkali solution by dissolving the alkali imparting agent in the first solvent (S10-2), and synthesizing the compound of the gibbsite structure by contacting the first metal salt solution and the alkali solution at room temperature (S10-3).

Process (S20) may include preparing a mixture by mixing the compound of the gibbsite structure, the divalent metal cation source, the dicarboxylic acid, and the second solvent (S20-1), and synthesizing an organic-inorganic hybrid compound by heating the mixture at a temperature of about 50° C. to about 90° C. and maintaining the temperature for about 3 hours to about 72 hours (S20-2).

Another aspect of the invention provides an organic-inorganic hybrid compound including:

two inorganic material layers, each extending in one direction and facing each other; and an organic material layer disposed between the two inorganic material layers, wherein each of the inorganic material layers has a gibbsite structure in which a divalent metal cation is doped to an octahedral site, and the organic material layer includes a plurality of pillar portions, each of which is chemically bound to each of the two inorganic material layers such that the two inorganic material layers are connected to each other.

The organic material layer may include a plurality of pillar portions disposed between the two inorganic material layers, the pillar portions extending in a direction perpendicular to a direction in which the two inorganic material layers extend.

The doped divalent cation may coordinate with all six oxygen atoms present around the octahedral site in the inorganic material layer, and may also be bound to anions present in the organic material layer by electrostatic attraction.

The organic material layer may form a hydrogen bond with each of the inorganic material layers.

The organic-inorganic hybrid compound may be represented by Formula 1:

[Formula 1]

In the formula, $M^{(II)}$ is a divalent metal cation, $M^{(III)}$ is a trivalent metal cation, $A^{2-}$ is a dicarboxylate ion, and x satisfies the condition of 0<x<0.2.

In Formula 1, x may satisfy the condition of 0.03≤x≤0.150.

$M^{(II)}$ may include $Zn^{2+}$, $Mn^{2+}$, $Co^{2+}$, $Ni^{2+}$, $Cu^{2+}$, $Mg^{2+}$, $Ca^{2+}$, $Sr^{2+}$, $Ba^{2+}$, or a combination thereof.

$M^{(III)}$ may include $Al^{3+}$, $Fe^{3+}$, $Cr^{3+}$, $B^{3+}$, $Ga^{3+}$, $In^{3+}$, $Y^{3+}$, or combination thereof.

$A^{2-}$ may include a divalent anion derived from terephthalic acid, oxalic acid, malonic acid, succinic acid, glutaric acid, 2-methylglutaric acid, 3-methylglutaric acid, adipic acid, pimelic acid, suberic acid, azelaic acid, sebacic acid, undecanedioic acid, dodecanedioic acid, brassylic acid, tetradecanedioic acid, fumaric acid, 2,2-dimethylglutaric acid, maleic acid, acetylenedicarboxylic acid, glutaconic acid, 2-disendioic acid, traumatic acid, muconic acid, glutinic acid, citraconic acid, mesaconic acid, itaconic acid, tartronic acid, mesosalic acid, malic acid, tartaric acid, oxalacetic acid, aspartic acid, glutamic acid, diaminopimelic acid, saccharic acid, 2,6-naphthalenedicarboxylic acid, or combination thereof.

The organic-inorganic hybrid compound may have the pillar density of about 1 pillar/(360 Å$^2$) to about 1 pillar/(55 Å$^2$), wherein the pillar density is represented by Equation 1:

Pillar density=the total number of pillar portions in a single organic material layer/planar surface area of a single inorganic material layer   [Equation 1]

The organic-inorganic hybrid compound may have the pillar density of about 1 pillar/(306 Å$^2$) to about 1 pillar/(74 Å$^2$), wherein the pillar density is represented by Equation 1

The average distance between adjacent pillar portions in the organic material layer may be from about 8.0 Å to about 20.6 Å.

The average distance between adjacent pillar portions in the organic material layer may be from about 9.2 Å to about 18.8 Å.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
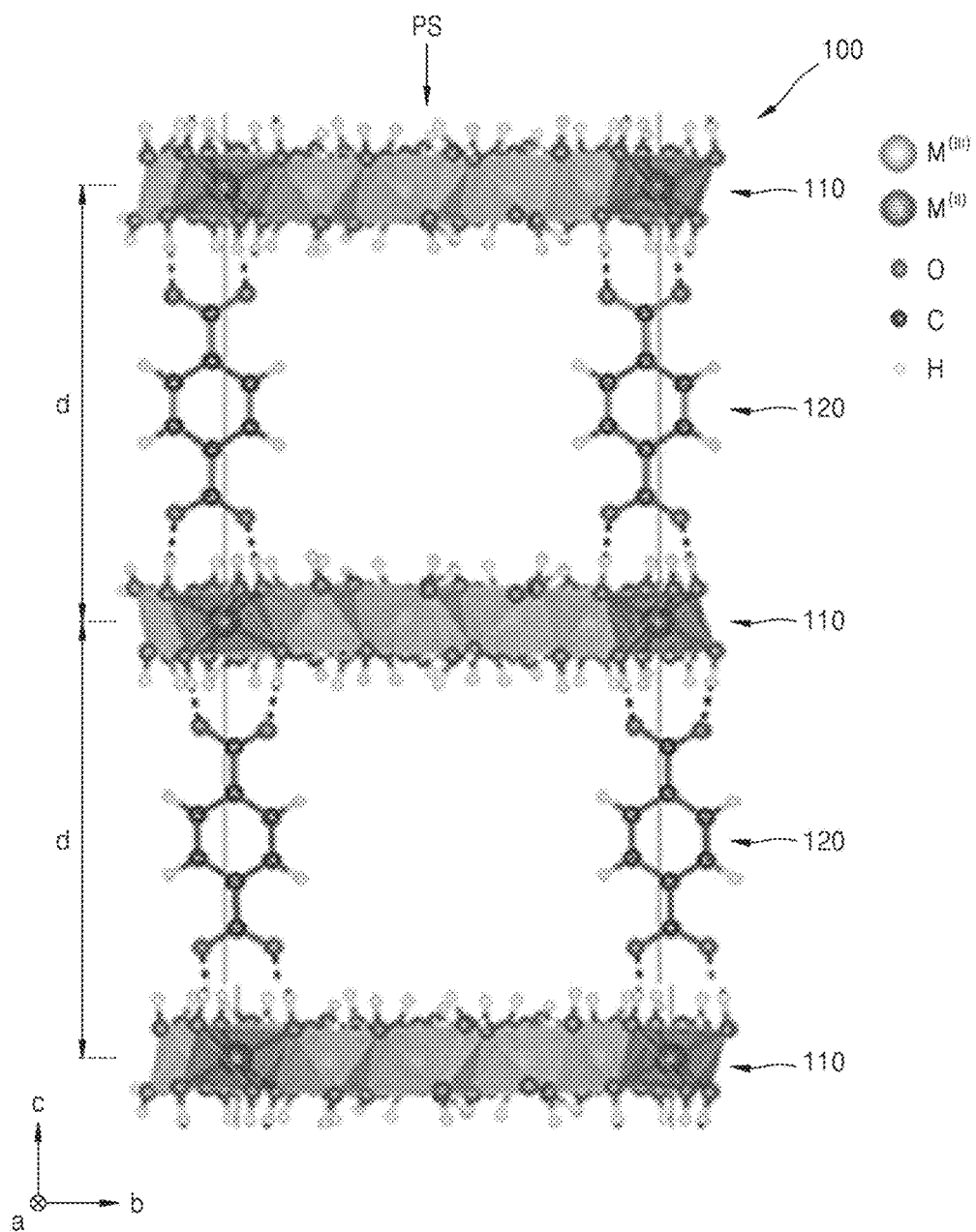
FIGS. 1A to 1C are schematic views illustrating an example of an organic-inorganic hybrid compound according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a method of preparing a sparsely pillared organic-inorganic hybrid compound according to an embodiment of the present disclosure will be described in detail.

The term "gibbsite structure" as used herein refers to a gibbsite ($Al(OH)_3$) structure itself, or any structure that is similar to that of gibbsite although components thereof are different from those of gibbsite (for example, a trivalent metal cation in place of Al).

The term "planar surface area" as used herein refers to the surface area of the smooth surface (that is, PS in FIG. 1A) of an organic-inorganic hybrid compound when the organic-inorganic hybrid compound is observed from above.

The term "the thickness of a single layer of an organic-inorganic hybrid compound (d)" as used herein refers to a distance between the centers of thicknesses of two adjacent inorganic material layers.

The term "hydrothermal synthesis method" as used herein refers to a synthesis method which is performed at a temperature higher than the boiling point of a solvent. Accordingly, when water is used as a solvent, a synthesis method which is performed at a temperature higher than 100° C., which is the boiling point of water, is referred to as "a hydrothermal synthesis method." In a hydrothermal synthesis method, since a closed vessel (autoclave) is used to apply a temperature higher than the boiling point of the solvent, in general, the air pressure in the reaction vessel is greater than 1 atm.

The term "a method other than a hydrothermal synthesis method" as used herein refers to a synthesis method which is performed at a temperature equal to or lower than the boiling point of a solvent. Accordingly, when water is used as a solvent, a synthesis method which is performed at a temperature equal to or lower than 100° C., which is the boiling point of water, is referred to as "a method other than a hydrothermal synthesis method."

The term "room temperature" as used herein refers to the temperature of about 10° C. to about 40° C. (for example, 25° C.).

The term "nominal value" or "nominal molar ratio" as used herein refers to a molar ratio of components used in the preparation of a sparsely pillared organic-inorganic hybrid compound.

The term "actual molar ratio" as used herein refers to a molar ratio of components contained in the finally prepared sparsely pillared organic-inorganic hybrid compound.

A method of preparing an organic-inorganic hybrid compound according to an embodiment of the present disclosure includes preparing a compound having a gibbsite structure by a method other than a hydrothermal synthesis method, using a trivalent metal cation source, an alkali imparting agent, and a first solvent (S10) and preparing an organic-inorganic hybrid compound by a method other than a hydrothermal synthesis method, using the compound of the gibbsite structure, a divalent metal cation source, dicarboxylic acid, and a second solvent (S20).

The trivalent metal cation source may be a source of a trivalent metal cation including $Al^{3+}$, $Fe^{3+}$, $Cr^{3+}$, $B^{3+}$, $Ga^{3+}$, $In^{3+}$, $Y^{3+}$ or a combination thereof.

The divalent metal cation source may be a source of a divalent metal cation including $Zn^{2+}$, $Mn^{2+}$, $Co^{2+}$, $Ni^{2+}$, $Cu^{2+}$, $Mg^{2+}$, $Ca^{2+}$, $Sr^{2+}$, $Ba^{2+}$, or a combination thereof.

The alkali imparting agent may include NaOH, LiOH, KOH, $LiBH_4$, $NaBH_4$, $KBH_4$, LiH, NaH, $LiAlH_4$, $NaAlH_4$, $KAlH_4$, $(i-Bu_2AlH)_2$, $LiHCO_3$, $NaHCO_3$, $KHCO_3$, $Li_2CO_3$, $Na_2CO_3$, $K_2CO_3$, $NH_4OH$, or a combination thereof.

The first solvent or the second solvent may include water.

Figure 8A:
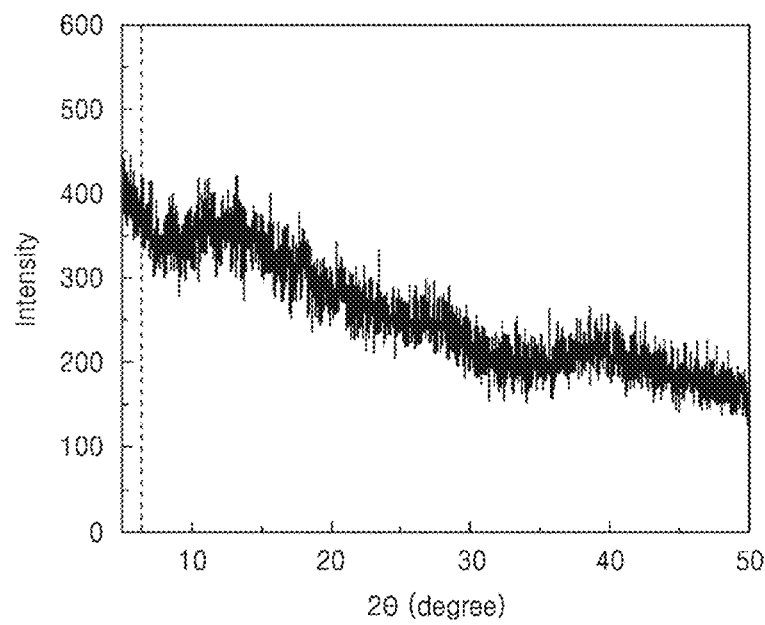
FIGS. 8A and 8B are XRD graphs of final compounds prepared in Comparative Examples 1 and 2 by a method other than a hydrothermal synthesis method, by using gibbsite prepared by a method other than a hydrothermal synthesis method.
Figure 8B:
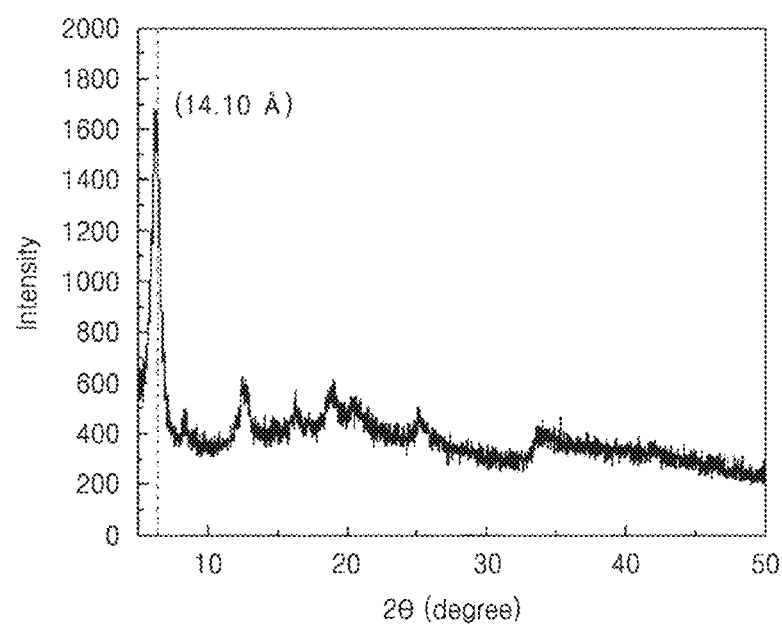
Figure 8C:
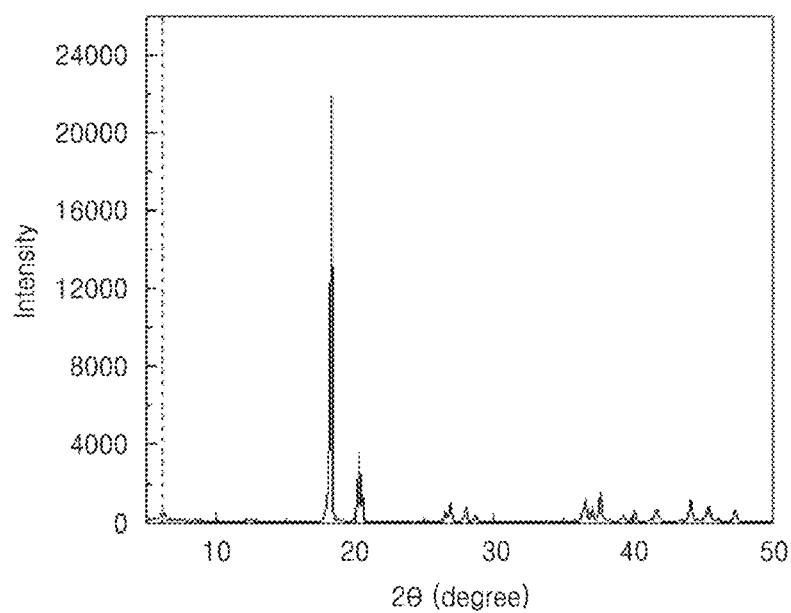
FIG. 8C is an XRD graph of a final compound prepared in Comparative Example 3 by a method other than a hydrothermal synthesis method, by using gibbsite prepared by a hydrothermal synthesis method.

The compound of the gibbsite structure may be prepared as an amorphous form from an X-ray diffraction (XRD) analysis result since the crystal thereof does not grow to a sufficient size in process (S10). Otherwise, when, instead of process (S10), a hydrothermal synthesis method is used to prepare a compound having the gibbsite structure, the obtained compound of the gibbsite structure has a strong crystallinity, and when an organic-inorganic hybrid compound is prepared by using such a compound, the dicarboxylic acid and the divalent metal cation may not be easily inserted into the compound. Accordingly, the sparsely pillared organic-inorganic hybrid compound 100 having the above-described configuration may not be obtained (see Comparative Examples 3 and FIG. 8C).

The meaning of "amorphous gibbsite" in process (S10) is as follows: that is, the structure of the compound obtained in the process (S10) is locally a gibbsite ($Al(OH)_3$)-like structure (for example, Al atoms form a hexagonal honeycomb structure, and around the empty space at the center thereof, six oxygen atoms form an octahedron), this structure can still be called a gibbsite structure. However, from the XRD's perspective of exploring the crystal structure, it is "amorphous". That is, since the crystal of the gibbsite particles did not grow to a sufficient size, the leftmost main peak representing the XRD of the gibbsite crystal (approximately 18.2° in angular position) disappeared, and other peaks were not clearly visible either, so the term "amorphous" is used.

The dicarboxylic acid may include terephthalic acid, oxalic acid, malonic acid, succinic acid, glutaric acid, 2-methylglutaric acid, 3-methylglutaric acid, adipic acid, pimelic acid, suberic acid, azelaic acid, sebacic acid, undecanedioic acid, dodecanedioic acid, brassylic acid, tetradecanedioic acid, fumaric acid, 2,2-dimethylglutaric acid, maleic acid, acetylenedicarboxylic acid, glutaconic acid, 2-disendioic acid, traumatic acid, muconic acid, glutinic acid, citraconic acid, mesaconic acid, itaconic acid, tartronic acid, mesosalic acid, malic acid, tartaric acid, oxalacetic acid, aspartic acid, glutamic acid, diaminopimelic acid, saccharic acid, 2,6-naphthalenedicarboxylic acid, or a combination thereof.

Process (S10) may include preparing a first metal salt solution by dissolving the trivalent metal cation source in the first solvent (S10-1), preparing an alkali solution by dissolving the alkali imparting agent in the first solvent (S10-2), and synthesizing the compound of the gibbsite structure by mixing the first metal salt solution and the alkali solution at room temperature (S10-3).

In one or more embodiments, process (S10) may further include, after process (S10-3), separating the prepared compound of the gibbsite structure via a solid-liquid separation (S10-4), washing the separated compound of the gibbsite structure (S10-5), and drying the washed compound of the gibbsite structure (S10-6).

Process (S20) may include preparing a mixture by mixing the compound of the gibbsite structure, the divalent metal cation source, the dicarboxylic acid, and the second solvent (S20-1), and synthesizing an organic-inorganic hybrid compound by heating the mixture at a temperature of about 50° C. to about 90° C. and maintaining the temperature for about 3 hours to about 72 hours (S20-2).

Ultimately, process (S20) is a process of intercalating a small amount of divalent metal cation and dicarboxylic acid into the compound of the gibbsite structure prepared according to process (S10), and in this process, the basic structure of the compound of the gibbsite structure is unchanged. Therefore, the inorganic material layer of the organic-inorganic hybrid compound synthesized in the process (S20) still has a gibbsite structure. In addition, the intercalated dicarboxylate ions combine with the inorganic material layer to promote crystal growth to a large size, thereby clearly showing the gibbsite crystal structure pattern with increased interlayer spacing in the XRD analysis.

Figure 8D:
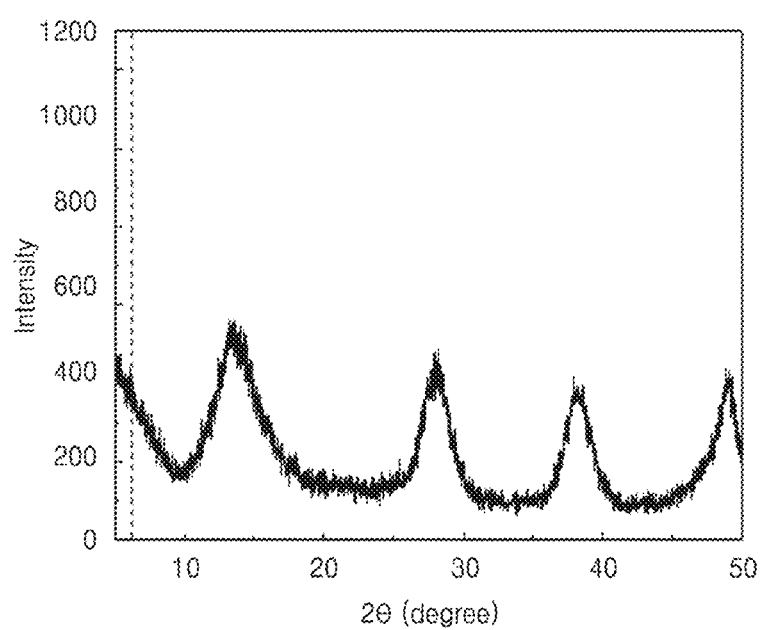
FIG. 8D is an XRD graph of a final compound prepared in Comparative Example 4 by a hydrothermal synthesis method, by using gibbsite prepared by a method other than a hydrothermal synthesis method.

Unlike in the process (S20), when an organic-inorganic hybrid compound is prepared by a hydrothermal synthesis method using gibbsite prepared by using a method other than a hydrothermal synthesis method in the process (S10), the structure is changed due to high temperature during hydrothermal synthesis, and thus the organic-inorganic hybrid compound 100 having the above-described configuration may not be obtained (see Comparative Example 4 and FIG. 8D).

In one or more embodiments, process (S20) may further include, after process (S20-2), separating the prepared compound of the gibbsite structure via a solid-liquid separation (S20-3), washing the separated compound of the gibbsite structure (S20-4), and drying the washed compound of the gibbsite structure (S20-5).

process (S10-4) and process (S20-3) may each be performed using a centrifuge.

In one or more embodiments, process (S10-5) and process (S20-4) may each be performed using distilled water.

In one or more embodiments, process (S10-6) and process (S20-5) may be performed by lyophilization.

The key feature of the sparsely pillared organic-inorganic hybrid compound to be achieved according to the present disclosure is to have a gibbsite structure. In process (S10) described above, which is also referred to as the former process, since only a trivalent metal cation (for example, $Al^{3+}$) and a hydroxyl group (OH— group) are added, it is obvious and is easily identified that there is a gibbsite $(Al(OH)_3)$-like structure. On the other hand, in process (S20), which is also referred to as the latter process, a divalent metal cation (for example, $Zn^{2+}$) is added. It is generally known that there could be a gibbsite structure and a hydrotalcite structure when a trivalent metal cation and divalent metal cation coexist (prior art documents 1 and 2). However, the sparsely pillared organic-inorganic hybrid compound of the present disclosure in which the divalent metal cation is less than 20 mol % of the total metal amount does not have a hydrotalcite structure and maintains only a gibbsite structure, which is obvious from the descriptions and examples presented below.

Hereinafter, a sparsely pillared organic-inorganic hybrid compound according to an embodiment of the present disclosure will be described in detail with reference to the drawings.

Figure 1B:
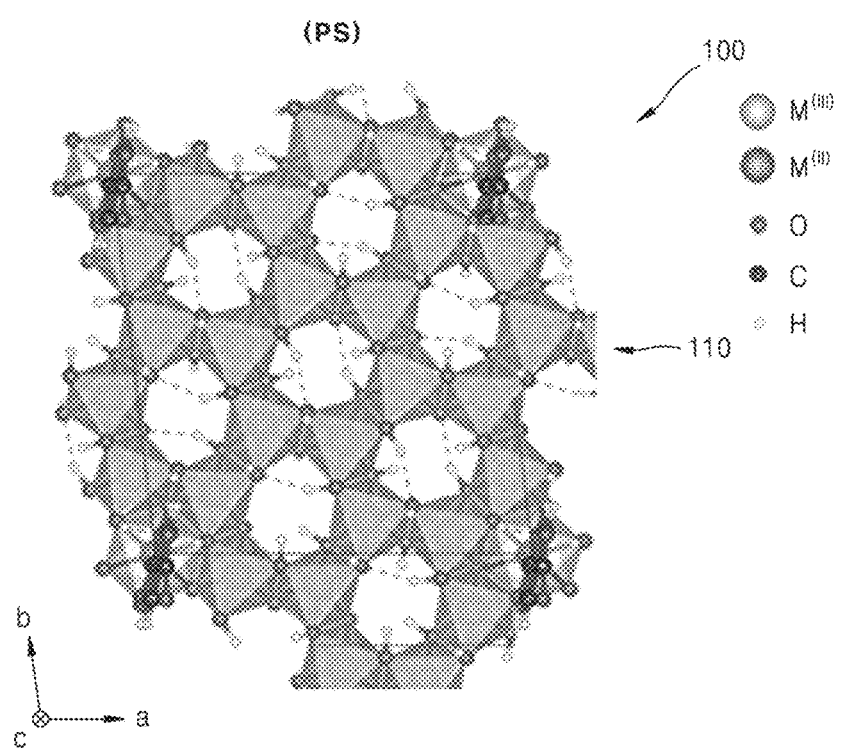
Figure 1C:
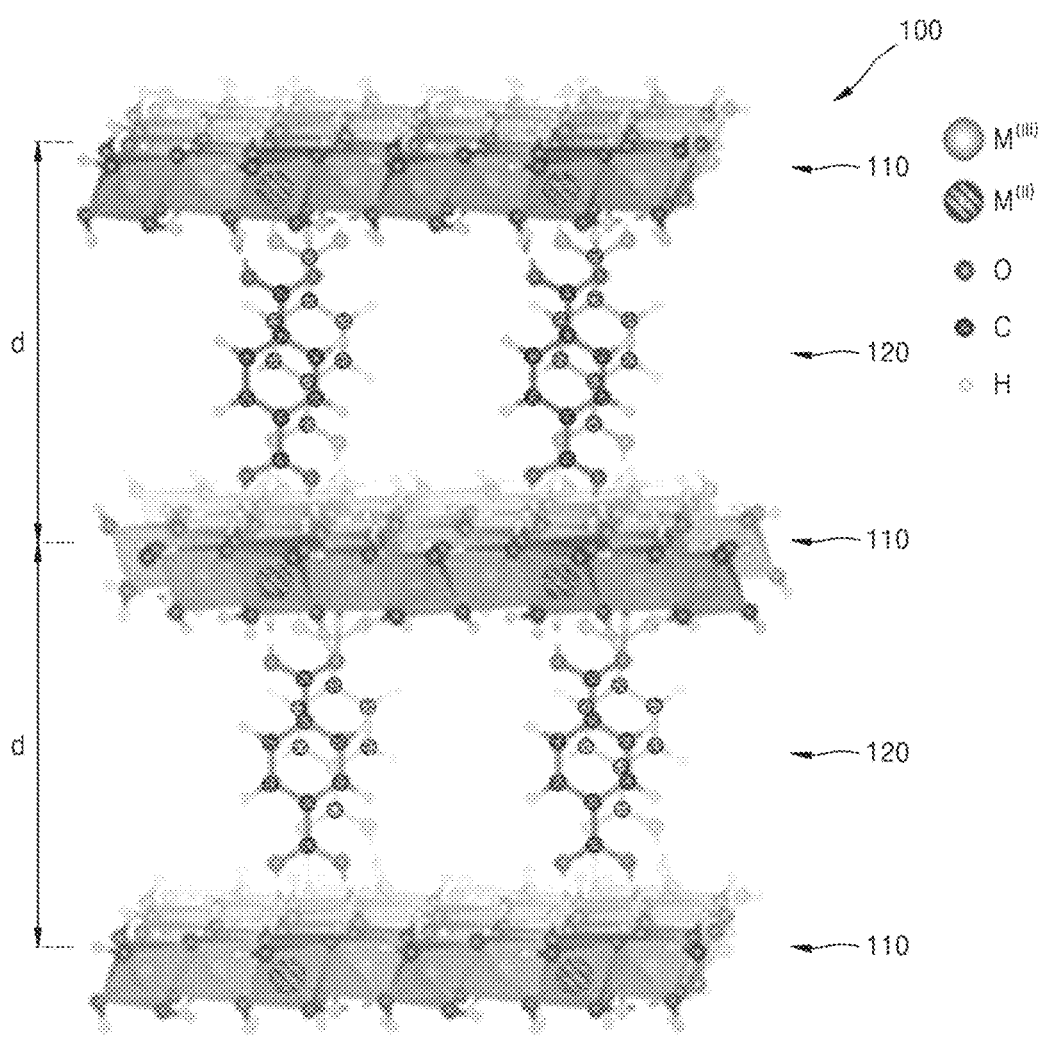

FIGS. 1A to 1C are schematic views illustrating an example of an organic-inorganic hybrid compound 100 according to an embodiment of the present disclosure. FIG. 1A is a side view, FIG. 1B is a plan view, and FIG. 1C is a perspective view. Specifically, FIGS. 1A to 1C illustrate unit cells of the organic-inorganic hybrid compound 100 (the thin solid black line in FIGS. 1A and 1B defines one unit cell), and in the case of the actual material, these unit cells are arranged repeatedly in the x, y, and z axes (a, b, and c axes in the drawing).

Referring to FIGS. 1A to 1C, the organic-inorganic hybrid compound 100 according to an embodiment of the present disclosure includes two inorganic material layers 110 and an organic material layer 120.

In detail, the organic-inorganic hybrid compound 100 may include at least two inorganic material layers 110 and at least one organic material layer 120 intercalated therebetween.

In one or more embodiments, in the organic-inorganic hybrid compound 100, a plurality of inorganic material layers 110 and a plurality of organic material layers 120 may be stacked alternately one on top of the other.

The two inorganic material layers 110 may be disposed to extend in one direction while facing each other.

In one or more embodiments, each of the inorganic material layers 110 may have a gibbsite structure in which a divalent metal cation is doped to an octahedral site.

The divalent cation may coordinate with all six oxygen atoms present around the octahedral site, and may also be bound to anions present in the organic material layer 120 by electrostatic attraction.

The organic material layer 120 may include a plurality of pillar portions intercalated between the two inorganic material layers 110. The pillar portions may extend in a direction crossing the direction in which the inorganic material layers 110 extend. For example, the organic material layer 120 may include a plurality of pillar portions disposed between the two inorganic material layers 110. The pillar portions may extend in a direction perpendicular to the direction in which the inorganic material layers 110 extend. As described above, when the organic material layer 120 includes a plurality of pillar portions disposed to extend in a direction perpendicular to the direction in which the inorganic material layers 110 extend between the two inorganic material layers 110, the empty space between the two inorganic material layers 110 expands so that molecules from outside can move promptly into the organic-inorganic hybrid compound 100 and also, the size and amount of the molecules that can diffuse thereinto may be increased.

In addition, the organic material layer 120 may include a plurality of pillar portions that are chemically bound to each of the two inorganic material layers 110 and thus connect the two inorganic material layers 110 to each other. In detail, when the two inorganic material layers 110 include a first inorganic material layer 110 and a second inorganic material layer 110 disposed to face each other, the organic material layer 120 may include a plurality of pillar portions, each having one end that is chemically bound to the first inorganic material layer 110 and the other end that is chemically bound to the second inorganic material layer 110. In more detail, the organic material layer 120 may include a plurality of pillar portions. Each of the pillar portions has one end and the other end which form hydrogen bonds with each of the inorganic material layers 110. Besides, as described above, divalent anions present in the organic material layer 120 are bound to the divalent cations doped to the octahedral sites of the inorganic material layers 110 by electrostatic attraction. Therefore, since the organic material layer 120 is firmly bound to each of the inorganic material layers 110, the organic-inorganic hybrid compound 100 may have a strong structure.

In addition, the organic molecules forming the pillar portions do not need to be perfectly periodically distributed, and in fact, the distances between the pillar portions can have a certain probability distribution. Despite this probability distribution, there is no difference in performance and structural stability.

In FIGS. 1A to 1C, the organic material layer 120 is illustrated as including divalent anions derived from terephthalic acid, but the present disclosure is not limited thereto.

In addition, the organic-inorganic hybrid compound 100 may be represented by Formula 1.

$$[M^{(II)}{}_x M^{(III)}(OH)_3]^{2x+}(A^{2-})_x \qquad \text{[Formula 1]}$$

In the formula, $M^{(II)}$ is a divalent metal cation, $M^{(III)}$ is a trivalent metal cation, $A^{2-}$ is a dicarboxylate ion, and x satisfies the condition of $0<x<0.2$.

In Formula 1, $[M^{(II)}{}_x M^{(III)}(OH)_3]^{2x+}$ may form the inorganic material layers 110 having the gibbsite structure, and $(A^{2-})_x$ may form the organic material layer 120.

$M^{(II)}$ may be doped to the octahedral site of the gibbsite structure.

In one or more embodiment, $M^{(II)}$ may coordinate with all six oxygen atoms present around the octahedral site, and may also be bound to anions ($A^{2-}$) present in the organic material layer 120 by electrostatic attraction.

In one or more embodiments, $M^{(II)}$ may include $Zn^{2+}$, $Mn^{2+}$, $Co^{2+}$, $Ni^{2+}$, $Cu^{2+}$, $Mg^{2+}$, $Ca^{2+}$, $Sr^{2+}$, $Ba^{2+}$, or a combination thereof.

$M^{(III)}$ may be a metal constituting the basic structure of gibbsite.

In one or more embodiments, $M^{(III)}$ may include $Al^{3+}$, $Fe^{3+}$, $Cr^{3+}$, $B^{3+}$, $Ga^{3+}$, $In^{3+}$, $Y^{3+}$, or a combination thereof.

One end and the other end of $A^{2-}$ (in detail, of which the total of four oxygen atoms, two of which are present at one end and the other two at the other end) may form a hydrogen bond with the inorganic material layers 110 (in detail, the total of four hydrogen atoms, two of which are present in the upper layer and the other two in the lower layer).

In one or more embodiments, $A^{2-}$ may include a divalent anion derived from terephthalic acid, oxalic acid, malonic acid, succinic acid, glutaric acid, 2-methylglutaric acid, 3-methylglutaric acid, adipic acid, pimelic acid, suberic acid, azelaic acid, sebacic acid, undecanedioic acid, dodecanedioic acid, brassylic acid, tetradecanedioic acid, fumaric acid, 2,2-dimethylglutaric acid, maleic acid, acetylenedicarboxylic acid, glutaconic acid, 2-disendioic acid, traumatic acid, muconic acid, glutinic acid, citraconic acid, mesaconic acid, itaconic acid, tartronic acid, mesosalic acid, malic acid, tartaric acid, oxalacetic acid, aspartic acid, glutamic acid, diaminopimelic acid, saccharic acid, 2,6-naphthalenedicarboxylic acid, or combination thereof.

Regarding Formula 1, the sparsely pillared organic-inorganic hybrid compound 100, satisfying the condition of $0<x<0.2$, may have the gibbsite structure, but cannot have the hydrotalcite structure. This is because: (1) in general, the hydrotalcite structure includes a divalent metal cation as a major component, some of which are substituted with a trivalent metal cation, in which, typically, the molar ratio of the divalent metal cation to the trivalent metal cation is 3:1 (that is, the proportion of the trivalent metal cation is 25 mol % of the metal). However, in the organic-inorganic hybrid compound 100 according to the present disclosure, the inorganic material layers 110 has at least 80 mol % of the trivalent metal cation and a very small amount (less than 20 mol %) of the divalent metal cation. Accordingly, the organic-inorganic hybrid compound 100 cannot have the hydrotalcite structure. (2) If the inorganic material layers 110 are assumed to have the hydrotalcite structure, since a trivalent metal cation has a positive charge value (3+), which is greater than that of a divalent metal cation (+2) by one, the neutralizing anion needs to be intercalated. However, like the organic-inorganic hybrid compound 100 according to the present disclosure, when the x value is very small (that is, $0<x<0.2$) and the trivalent metal cation occupies 80 mol % or more, the amount of anions required to make the total material neutral is excessively high, and thus, even when the entire interlayer space is filled up with anions, there are still a need for space to be filled with anions. Accordingly, this assumption is impossible to be implemented.

In detail, in Formula 1, x may satisfy the condition of $0.03 \le x \le 0.150$.

Regarding Formula 1, when x is less than 0.03, the density of the organic material layer 120 of the organic-inorganic hybrid compound 100 is too low, the pillar structure may not be maintained, and when x is greater than 0.150, the density of the organic material layer 120 of the organic-inorganic hybrid compound 100 is too high, the speed of molecules diffusing into the organic-inorganic hybrid compound 100 may be decreased and the size and amount of diffusible molecules may be decreased. In detail, for the organic-inorganic hybrid compound 100 of the present disclosure to be an excellent molecular adsorbent, molecules need to be easily and quickly moved (that is, diffused) between layers, and the limiting condition therefor is that individual pillar portions (that is, $A^{2-}$ anions disposed perpendicular to the direction in which the organic material layer 120 extends) should not stick together in any (a-axis or b-axis) directions (see FIG. 1B). When the pillar density increases and a growing number of pillar portions stick together sporadically in space, the molecular movement through those regions is obstructed and thus the molecular diffusion is accordingly reduced.

In the organic-inorganic hybrid compound 100, if x equals ½, the situation corresponds to the case where the pillars fill all possible positions (shown as white hexagons in FIG. 1B) and all pillars stick together completely. On the other hand, if x equals 0.125, the situation corresponds to the case where the pillars fill only half of the possible positions along the a-axis direction and the same along the b-axis direction (that is, every other position is empty, avoiding the sticking of pillars). As the x value is increased to be greater than 0.125, the sticking of pillars must occur to accommodate the given number of pillars and the molecular movement is significantly limited, and when the x value reaches 0.2, the efficiency of molecular adsorption or storage becomes extremely low.

Figure 2:
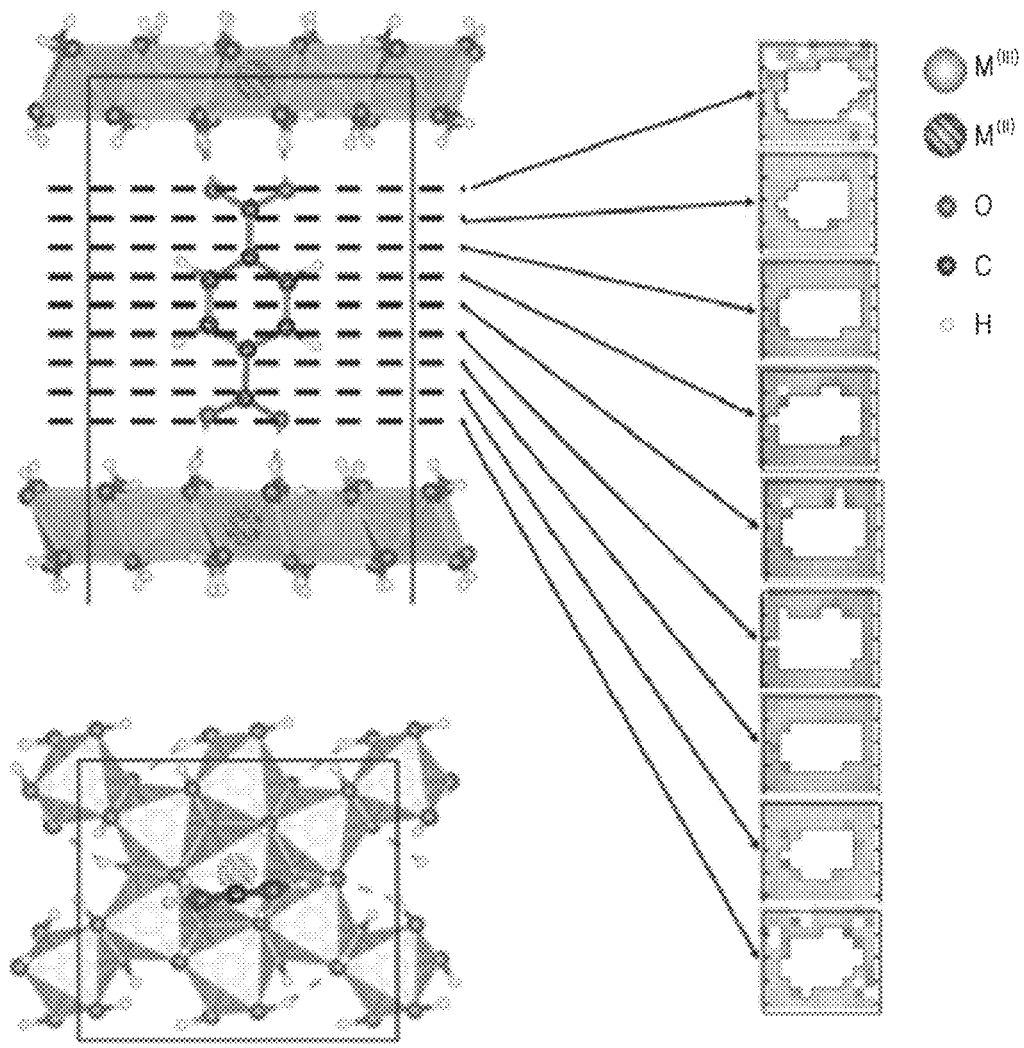
FIG. 2 is a diagram showing, in pixel form, regions in which molecules introduced from the outside are unable to access due to spatial repulsion in an organic-inorganic hybrid compound according to an embodiment of the present disclosure.

To identify how much the adsorption or storage ability is reduced due to the filling of space by pillar portions, a quantitative calculation method was adopted. Using the methods of reference documents 1 and 2, which are widely used in the theoretical physical chemistry, when $M^{(II)}=Zn^{2+}$, $M^{(III)}=Al^{3+}$, $A^{2-}$=terephthalate ion $(C_8H_4O_4^{2-})$, and nominal x=0.125, the energy of the hydrogen molecule ($H_2$), which was introduced from the outside, interacting with the organic-inorganic hybrid compound was calculated at all points in the space. The region, of which the interaction energy has a positive value, acts as an energy barrier, and the hydrogen molecule may not have an access thereto. That is, calculation was performed to find an inaccessible region where the molecule is not allowed to access due to a spatial exclusion between the organic-inorganic hybrid compound and the introduced molecule. The reason for selecting $H_2$ corresponding to the smallest molecule is to obtain the minimum value of the access exclusion region, and for larger molecules, the access exclusion region is further expanded. The space in the organic-inorganic hybrid compound 100 is subdivided into small sections, and the interaction energy between the hydrogen and the organic-inorganic hybrid compound when the hydrogen molecule is present in a specific section, is calculated, and the calculation is repeatedly performed for all sections. Results thereof are shown in FIG. 2. The interlayer space in the organic-inorganic hybrid compound is divided into 9 layers, which are indicated by doted lines, and the cross section of each layer is subdivided into small pixels in which the region with positive (+) energy is marked as white and the region with negative (−) energy is marked as gray. It can be seen from FIG. 2 that an average access exclusion region of 28.6 Å$^2$ is marked as white in each layer per a single pillar portion. The inaccessible white region has approximately an elliptical shape with an average radius of about 3.0 Å. The proportion of accessible gray regions on the cross section may be expressed as a function of x, that is, (1−2.6x). From this equation, the proportion of accessible region when nominal x=0.0625 is about 84%.

In one or more embodiments, the organic-inorganic hybrid compound 100 may have the pillar density of about 1 pillar/(360 Å$^2$) to about 1 pillar/(55 Å$^2$), wherein Å$^2$ is a square angstrom and the pillar density is represented by Equation 1:

Pillar density=the total number of pillar portions in a single organic material layer/planar surface area of a single inorganic material layer    [Equation 1]

In detail, the organic-inorganic hybrid compound 100 may have the pillar density of about 1 pillar/(306 Å$^2$) to about 1 pillar/(74 Å$^2$), wherein the pillar density is represented by Equation 1.

When the pillar density is less than 1 pillar/(306 Å$^2$), it is practically difficult to synthesize the pillar structure since the available amount of organic material $A^{2-}$ supporting the structure in the organic-inorganic hybrid compound 100 is too little, and with the pillar density of less than 1 pillar/(360 Å$^2$), the pillar structure may not even be realized. When the pillar density is greater than 1 pillar/(74 Å$^2$), the pillar density of the organic material layer 120 in the organic-inorganic hybrid compound 100 is so large that the diffusion of molecules into the organic-inorganic hybrid compound 100 is not only limited, but also the size and the amount of diffusible molecules are greatly reduced, and when the pillar density reaches 1 pillar/(55 Å$^2$), the efficiency of molecular adsorption or storage becomes extremely small.

The achievement of structural stability with such a low pillar density (down to 1 pillar/(360 Å$^2$)) is based on a newly established chemical bond in the organic-inorganic hybrid compound 100 of the present disclosure: (1) hydrogen bond formed by oxygen atoms at both ends of the dicarboxylate ion and hydrogen atoms on the surface of the inorganic material layer 110 having the gibbsite structure makes the greatest contribution, and there are four hydrogen bonds per dicarboxylate ion (two at one end of the dicarboxylate ion and two at the other end) (in FIG. 1A, the hydrogen bonds are indicated by dotted lines). (2) A divalent metal cation (for example, $Zn^{2+}$) enters an empty space in the center of the hexagon having, as its vertices, six trivalent metal cations (for example, $Al^{3+}$s) connected in the shape of a honeycomb (FIG. 1B) in the inorganic material layers 110 of the gibbsite structure, and is bound to a dicarboxylate anion (for example terephthalate ion: $(C_8H_4O_4)^{2-}$) intercalated between the inorganic material layers by electrostatic attraction, contributing to the structural stability. (3) The weak van der Waals interaction between the atoms of the inorganic material layers 110 having the gibbsite structure and the atoms that constitute the dicarboxylic acid makes an additional small contribution to the bond.

As a result, even if the density of pillars comprising dicarboxylate ions is small, a stable structure can be maintained.

The average distance between pillar portions adjacent to each other in the organic material layer 120 may be from about 8.0 Å to about 20.6 Å (angstrom).

In detail, the average distance between pillar portions adjacent to each other in the organic material layer 120 may be from about 9.2 Å to about 18.8 Å.

When the average distance between the pillar portions is less than 9.2 Å, the internal space in the organic-inorganic hybrid compound 100 is so small that the diffusion of molecules into the organic-inorganic hybrid compound 100 is not only restricted, but also the size and the amount of diffusible molecules may be largely reduced, and when the average distance is less than 8.0 Å, the efficiency of molecular adsorption or storage in the compound becomes extremely low. When the average distance between the pillar portions is greater than 18.8 Å, it is practically difficult to synthesize the pillar structure since the available amount of organic material layer $A^{2-}$ supporting the structure in the organic-inorganic hybrid compound 100 is too little, and when the average distance is greater than 20.6 Å, the pillar structure may not even be realized.

In one or more embodiments, the organic-inorganic hybrid compound 100 may be usefully used to adsorb and/or store various gases and metals.

When the organic-inorganic hybrid compound 100 of the present disclosure is used for molecular adsorption, hydroxyl groups (OH) exposed on the surface of the inorganic material layers 110 make the greatest contribution, and a material that forms a pillar and doped metal (dicarboxylate ions and divalent metal cations) also make an additional contribution. In one or more embodiments, the large specific surface area and the large pore volume play a decisive role in improving the adsorption ability.

For example, the organic-inorganic hybrid compound 100 may be useful to adsorb or store volatile organic compounds, environmentally harmful liquid materials that cause sick house syndrome, polycyclic aromatic hydrocarbons, exhaust gas-based environmental pollutants, greenhouse gases, radioactive substances, harmful heavy metals, toxic chemicals, and/or hydrogen.

The volatile organic compound may include benzene, toluene, xylene, or a combination thereof.

The environmentally harmful liquid materials may include formaldehyde, chloroform, or a combination thereof.

The polycyclic aromatic hydrocarbons, may include benzo(a)pyrene.

The exhaust gas-based environmental pollutant may include NO, $NO_2$, $N_2O$, $SO_2$, CO, or a combination thereof.

The greenhouse gas may include $CO_2$, $CH_4$, or a combination thereof.

The radioactive material may include cesium (Cs).

The harmful heavy metal may include Pb.

The toxic chemicals may include chlorine gas ($Cl_2$), phenol, hydrogen cyanide (HCN), acrolein, nicotine, or a combination thereof.

Hereinafter, the storage of hydrogen using the organic-inorganic hybrid compound 100 will be described in detail.

The biggest goal in the hydrogen storage is to safely store a large amount of hydrogen at room temperature. In the case of the hydrogen molecule ($H_2$), the absolute value of the hydrogen adsorption energy to the organic-inorganic hybrid compound 100 is much smaller (depending on adsorption sites, about 2 kJ/mol to about 10 kJ/mol or, equivalently, 20 meV (millielectron volts) to 100 meV per molecule) than that of the above-mentioned harmful materials (27 kJ/mol or more in Tables 7 and 8 described later). In fact, it is well known that it is extremely difficult to store hydrogen at room temperature by using any adsorbents studied previously (see reference document 3). At a very low temperature of $-196°$ C.(=77K), which is the nitrogen liquefaction temperature, hydrogen can in principle be stored in spite of the small adsorption energy magnitude, but such a low-temperature method is not economical at all. For this reason, hydrogen-fuel-cell-powered vehicles currently store hydrogen which has been compressed at a very high pressure of 700 atm in an empty hydrogen tank, without using any storage material, which raises a safety issue. The organic-inorganic hybrid compound 100 of the present disclosure may have an average magnitude of the adsorption energy greater than those of previously studied materials as described below, and due to the layered structure, it may have a relatively uniform adsorption energy value throughout the pores thereof and thus, may act as a potential well for storing hydrogen molecules. Accordingly, in the organic-inorganic hybrid compound 100 of the present disclosure, the density of hydrogen therein is increased, and synergistically with a very large pore volume, the hydrogen storage ability can be significantly improved even at room temperature.

Hereinafter, the principle in which the organic-inorganic hybrid compound 100 of the present disclosure adsorbs and stores hydrogen will be described in detail.

First, the organic-inorganic hybrid compound 100 of the present disclosure has many hydroxyl groups (OH) on the upper and lower surfaces of each of the inorganic material layers 110. In particular, oxygen has a strong negative charge, so a high electric field is formed in the vicinity thereof.

Therefore, the organic-inorganic hybrid compound 100 of the present disclosure uses this property to adsorb hydrogen better than a nonpolar material (that does not produce an electric field) such as activated carbon which is known to hardly adsorb hydrogen. When hydrogen is adsorbed on a material that does not form an electric field, the adsorption is made mainly by a very weak van der Waals interaction. However, when there is an electric field, although the electric dipole value (p) of the hydrogen molecule ($H_2$) is 0, the electric polarizability value (a) is $0.804 \times 10^{-24}$ $cm^3$ (see reference document 4), and the electric quadrupole value (Q) is $0.662 \times 10^{-26}$ $esu \cdot cm^2$ (see reference document 5), both of which contribute to adsorption.

The sizes of the electric field and the electric field gradient (E) near the oxygen constituting the organic-inorganic hybrid compound 100 were obtained by calculating the electronic structure in the organic-inorganic hybrid compounds prepared according to Example 1 by using the methods disclosed in reference documents 1 and 2. As a result, it was found that the electric field and the electric field gradient (E) were about 0.6 V/Å and 0.3 V/Å$^2$, respectively, at the position where molecules are adsorbed inside the material. The induced dipole energy and the quadrupole energy are each obtained using known equations $$\left( -1/2 \times \alpha \times E^2 \text{ and } -\frac{1}{6} \sum_i \sum_j Q_{ij} \frac{\partial E_j}{\partial x_i}(0) \right)$$

reference document 6), and as a result, it was found that the induced dipole and the quadrupole provide additional adsorption energy of $-10$ meV and $-20$ meV per hydrogen molecule, respectively, and the sum (about $-30$ meV) thereof contributes significantly to adsorption of hydrogen molecules at room temperature. In general, in the cryogenic experiment at 77K (=$-196°$ C.) absolute temperature, which has been performed in the past, adsorption storage is performed well without this additional adsorption energy contribution. However, at room temperature where the adsorption storage is poor in general, this additional adsorption energy ($-30$ meV) is very important, and due to the additional adsorption energy, the storage ability may be increased by about 3 times compared to when there is the van der Waals interaction alone. In detail, when the adsorption energy is added as much as $-30$ meV and thus there is the corresponding change ($\Delta \mu$) in the chemical potential $\mu$, the kT value at 25° C. (k is the Boltzmann constant, and T (absolute temperature)=298.15K) is 25.7 meV, and the density change factor according to equilibrium thermodynamics (reference document 7) is, exp ($-\Delta \mu/kT$)=3.2. In other words, the density of the gas to be stored is increased by about 3 times due to the electric field.

The sparsely pillared organic-inorganic hybrid compound 100 having the above-described configuration according to an embodiment of the present disclosure is a novel material that did not exist before the present disclosure, firstly discovered by the present inventors after hard work.

In one or more embodiments, in the sparsely pillared organic-inorganic hybrid compound 100 having the above-described configuration according to an embodiment of the present disclosure, organic material molecules, for example, dicarboxylate series (for example, $C_6H_4O_4$, that is, terephthalate) are inserted in the vertical pillar shape into between inorganic materials forming a layered structure, for example, layers of the gibbsite ($Al(OH)_3$) to form a structure in which inorganic materials are chemically bound to the organic material while obtaining a structural stability with a low pillar density. Moreover, by minimizing the density of the organic material existing as pillars between the inorganic material layers 110, the volume of the empty pores between the layers is maximized, so that a large amount of harmful materials or various gases can be captured and thus adsorbed or stored. In addition, the interlayer spacing is increased from 4.86 Å, which is the original distance of gibbsite, to 14.1 Å or more (in the case of terephthalate), thereby contributing to an increase in the pore volume.

Hereinafter, the present disclosure will be described using the following examples, but the present disclosure is not limited to the following examples.

EXAMPLES

Examples 1-5 and Comparative Examples 1 and 2: Preparation of Organic-Inorganic Hybrid Compounds (Preparation of gibbsite by method other than hydrothermal synthesis method)

$Al(NO_3)_3$ was completely dissolved in 250 ml water by stirring to prepare an $Al(NO_3)_3$ aqueous solution, and NaOH was completely dissolved in 250 ml water by stirring to prepare a NaOH aqueous solution.

Thereafter, the $Al(NO_3)_3$ aqueous solution (25° C.) and the NaOH aqueous solution (25° C.) were mixed to obtain a white precipitate.

Thereafter, water was first removed from the precipitate through a centrifuge, and the resultant was washed with distilled water three or more times to remove unreacted residue to obtain white powder.

Thereafter, the washed clean white powder was put in a lyophilizer and dried for about a week to obtain an amorphous gibbsite containing about 30% by weight of moisture.

In the preparation of gibbsite by the method other than a hydrothermal synthesis method, even when $AlCl_3$ or $Al_2(SO_4)_3$ was used instead of $Al(NO_3)_3$, the same amorphous gibbsite was obtained.

(Preparation of organic-inorganic hybrid compounds by method other than hydrothermal synthesis method)

Amorphous gibbsite containing about 30% by weight of moisture obtained above, $ZnCl_2$, and terephthalic acid were added to 200 ml of distilled water, heated to the temperature of 70° C., and maintained for 7 hours to obtain a precipitate.

Thereafter, water was first removed from the precipitate through a centrifuge, and the resultant was washed with distilled water once to obtain white powder.

Thereafter, the obtained white powder was dried by using a lyophilizer for 48 hours to obtain an organic-inorganic hybrid compound doped with Zn.

The types and amounts of the source materials and the nominal Zn/Al molar ratio among the source materials, used in Examples 1 to 5 and Comparative Examples 1 and 2, are summarized in Table 1 below.

TABLE 1

| | Source materials (g) | | | Nominal Zn/Al molar ratio among source materials |
|---|---|---|---|---|
| | $Al(OH)_3 \cdot 2H_2O$ | $ZnCl_2$ | Terephthalic acid | |
| Example 1 | 2.37 | 0.176 | 0.216 | 0.0625 |
| Example 2 | 2.37 | 0.152 | 0.184 | 0.0534 |
| Example 3 | 2 37 | 0.132 | 0 168 | 0.0468 |
| Example 4 | 2.37 | 0.117 | 0.144 | 0.0417 |
| Example 5 | 2.37 | 0.352 | 0.432 | 0.125 |
| Comparative Example 1 | 2.37 | 0 094 | 0.115 | 0.0333 |
| Comparative Example 2 | 2.37 | 0.563 | 0.691 | 0.2 |

Comparative Example 3: Preparation of Organic-Inorganic Hybrid Compound (Preparation of Gibbsite by Hydrothermal Synthesis Method)

$Al(NO_3)_3$ was completely dissolved in 250 ml water by stirring to prepare an $Al(NO_3)_3$ aqueous solution, and NaOH was completely dissolved in 250 ml water by stirring to prepare a NaOH aqueous solution.

Thereafter, the $Al(NO_3)_3$ aqueous solution and the NaOH aqueous solution were mixed, placed in a hydrothermal synthesis reactor (autoclave), heated to 120° C., and maintained for 6 hours to obtain a white precipitate.

Thereafter, water was first removed from the precipitate through a centrifuge, and the resultant was washed with distilled water once to remove unreacted residue to obtain white powder.

Thereafter, the washed clean white powder was put in a lyophilizer and dried for about 48 hours to obtain gibbsite with excellent crystallinity ($\gamma$-$Al(OH)_3$) containing about 30% by weight of moisture.

(Preparation of Organic-Inorganic Hybrid Compounds by Method Other than Hydrothermal Synthesis Method)

An organic-inorganic hybrid compound was obtained in the same manner as in Example 1 (that is, a method other than a hydrothermal synthesis method), except that crystalline $Al(OH)_3$ prepared by hydrothermal synthesis method in Comparative Example 3 was used instead of the amorphous $Al(OH)_3$ prepared by the method other than a hydrothermal synthesis method in Example 1.

Comparative Example 4: Preparation of Organic-Inorganic Hybrid Compound

An organic-inorganic hybrid compound was obtained in the same manner as in Example 1, except that, in the latter process for the preparation of an organic-inorganic hybrid compound, the hydrothermal synthesis method was used instead of the method other than a hydrothermal synthesis method.

In detail, the amorphous gibbsite prepared by using the method other than a hydrothermal synthesis method in Example 1, $ZnCl_2$, and terephthalic acid were added to 200 ml of distilled water, heated to 120° C. in a hydrothermal synthesis reactor (autoclave) and then maintained for 6 hours to obtain a precipitate.

Thereafter, water was first removed from the precipitate through a centrifuge, and the resultant was washed with distilled water once to obtain white powder.

Thereafter, the obtained white powder was dried by using a lyophilizer for 48 hours to obtain the final compound.

Evaluation Example 1: Analysis of XRD Graph of Gibbsite ($Al(OH)_3$)

Figure 3:
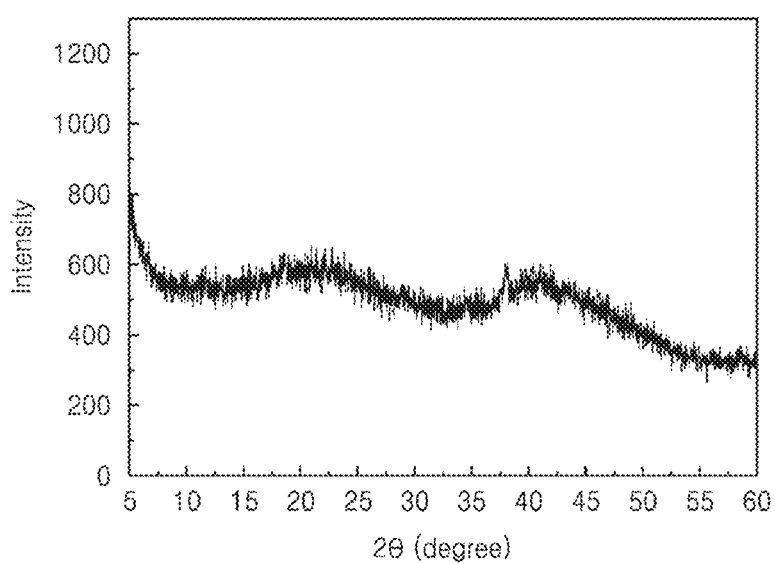
FIG. 3 is an X-ray diffraction (XRD) graph of gibbsite prepared in Example 1 by using a method other than a hydrothermal synthesis method.
Figure 4:
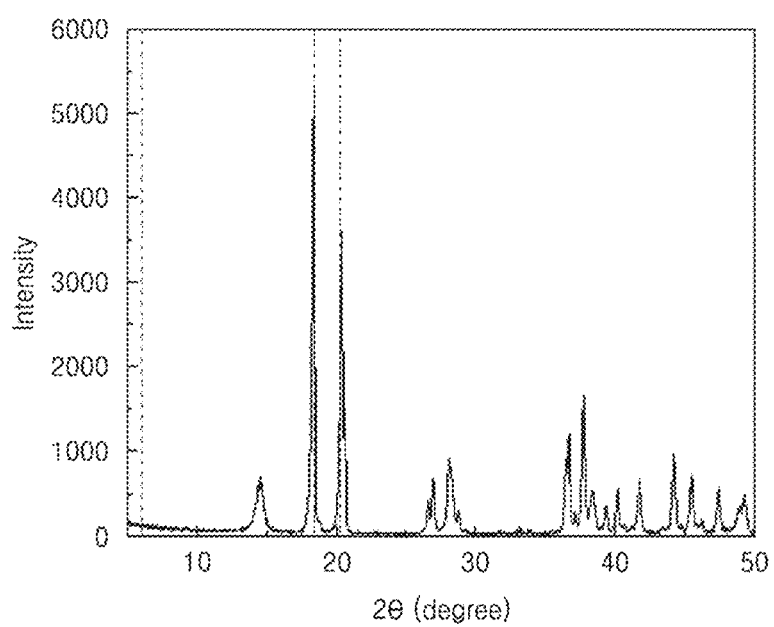
FIG. 4 is an XRD graph of gibbsite prepared in Comparative Example 3 by a hydrothermal synthesis method.

The XRD of gibbsite prepared according to the gibbsite preparation process (S10) in Example 1 is shown in FIG. 3 (Examples 2-5 and Comparative Examples 1 and 2 are exactly the same as Example 1 up to the gibbsite preparation process (S10)). The XRD graph of gibbsite prepared according to Comparative Example 3 is shown in FIG. 4. As the XRD device, D/Max-2500VK/PC of Rigaku was used, and the analysis conditions included the CuKα radiation speed of 2° $min^{-1}$.

Figure 5:
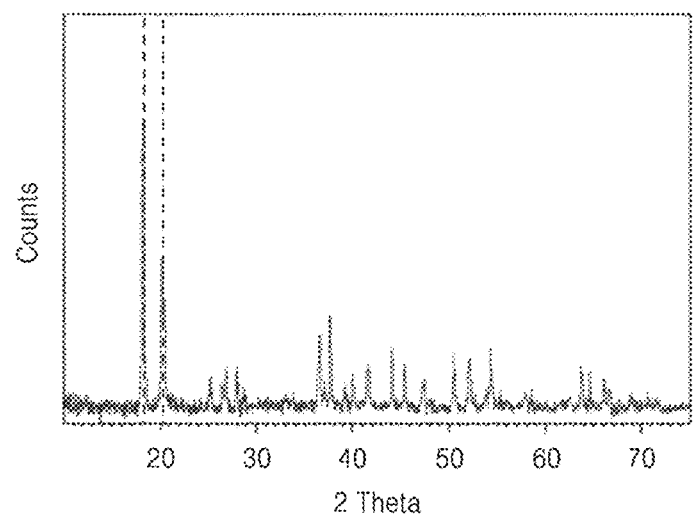
FIG. 5 is an XRD graph of the gibbsite crystal (γ-Al(OH)$_3$) disclosed in reference document 8.
Figure 6:
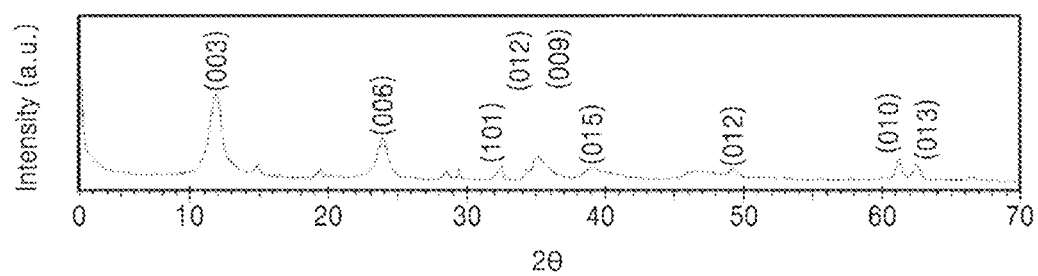
FIG. 6 is an XRD graph of hydrotalcite disclosed in reference document 9.
Figure 7A:
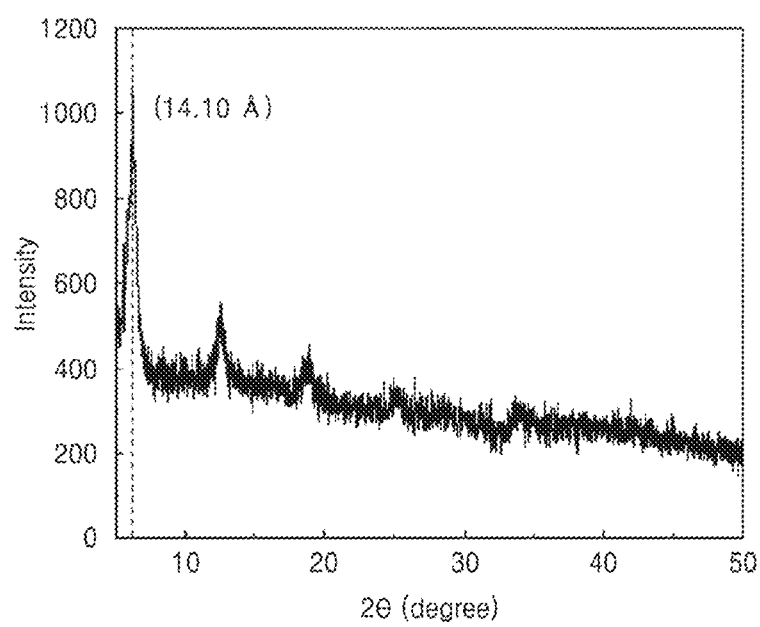
FIGS. 7A to 7E are XRD graphs of organic-inorganic hybrid compounds prepared in Examples 1 to 5 by a method other than a hydrothermal synthesis method, by using gibbsite prepared by a method other than a hydrothermal synthesis method.
Figure 7B:
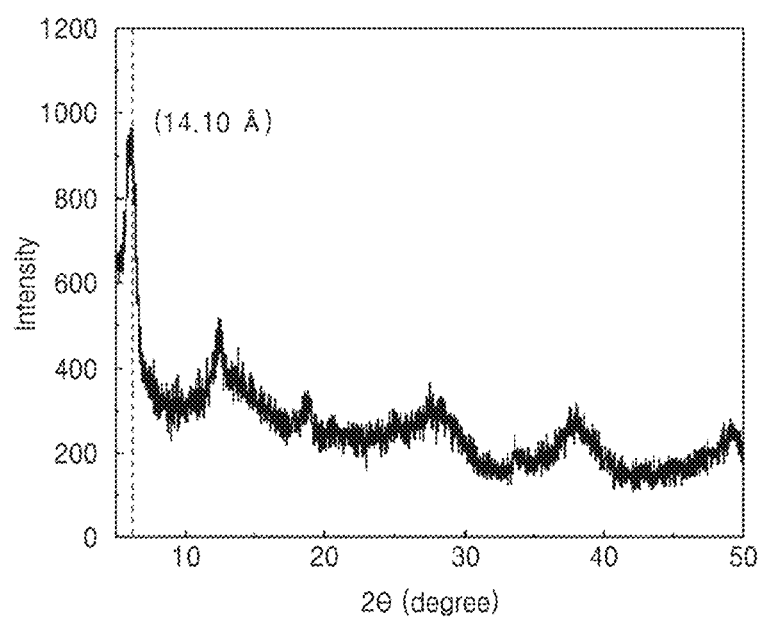
Figure 7C:
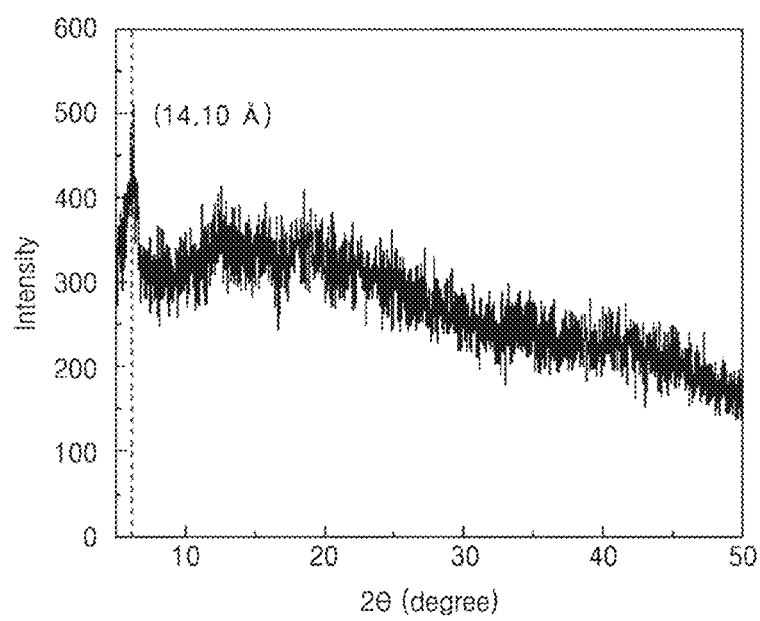
Figure 7D:
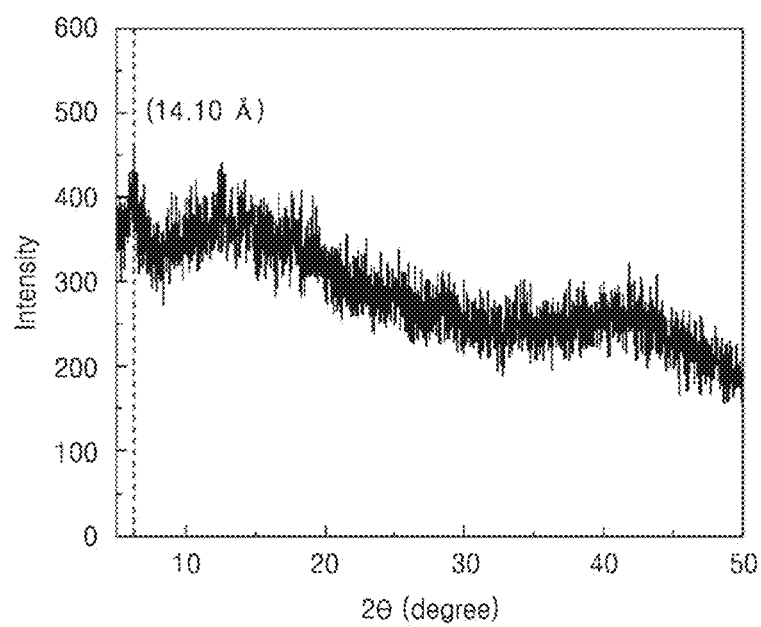
Figure 7E:
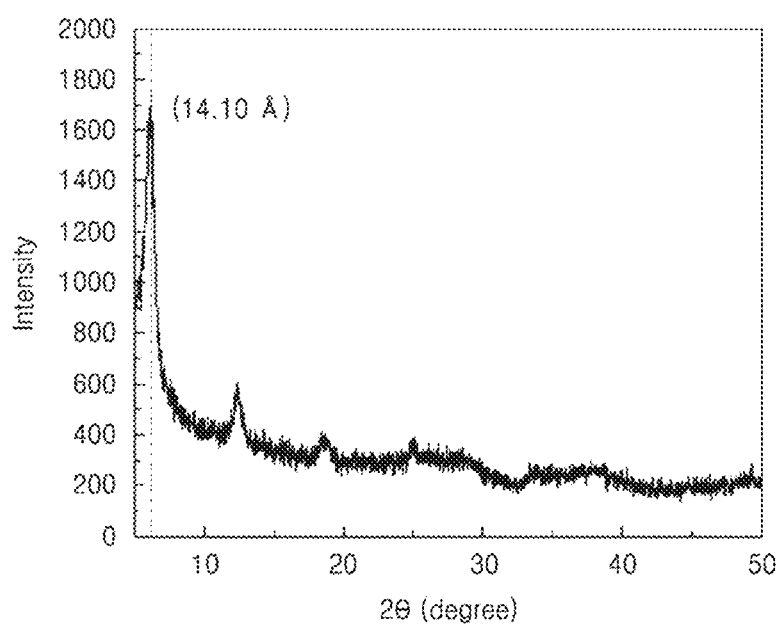

FIG. 5 is an XRD graph of typical gibbsite crystal structure ($\gamma$-$Al(OH)_3$) disclosed in reference document 8, and FIG. 6 is an XRD graph of hydrotalcite (a layered structure material containing Al and Mg) disclosed in reference document 9.

Referring to FIGS. 3 to 6, the XRD graph (Example 1) of FIG. 3 shows the typical pattern of an amorphous material in which no distinctively sharp XRD peaks are present. The ratio of Al:OH added in the gibbsite manufacturing process and the ratio of Al:O in EDX elemental analysis (H is generally excluded from the EDX analysis) were each 1:3, and in the component aspect, gibbsite ($Al(OH)_3$ was formed, but an amorphous form was obtained, which was different from those of FIGS. 4 to 6. The pattern of the XRD graph of FIG. 4 (Comparative Example 3) was similar to that of the XRD graph of the gibbsite crystal structure ($\gamma$-$Al(OH)_3$) disclosed in FIG. 5, and was completely different from that of the XRD graph of FIG. 6. From these results, it was confirmed that the putative gibbsite material prepared according to the former process in Example 1 and Comparative Example 3 was not hydrotalcite. In detail, it was confirmed that the putative gibbsite material prepared according to Example 1 is gibbsite in the component aspect, but has an amorphous gibbsite structure rather than the crystalline gibbsite structure, and the putative gibbsite material prepared according to Comparative Example 3 actually has a crystalline gibbsite structure.

Evaluation Example 2: Analysis of XRD Graph of Organic-Inorganic Hybrid Compound The XRD graphs of the organic-inorganic hybrid compounds produced in Examples 1 to 5 and Comparative Examples 1 to 4 were analyzed, and the results are sequentially shown in FIGS. 7A to 7E and 8A to 8D. As the XRD device, D/Max-2500VK/PC of Rigaku was used, and the analysis conditions included the CuK$\alpha$ radiation speed of 2° $min^{-1}$.

As described above, the finally prepared sparsely pillared organic-inorganic hybrid compound cannot have a hydrotalcite structure, but can have a gibbsite structure, because the proportion of a trivalent metal cation (for example, $Al^{3+}$) is overwhelmingly higher than that of the divalent metal cation (for example, $Zn^{2+}$). However, since the divalent anion (for example, terephthalate ions) is intercalated and acts as a pillar and thus the interlayer spacing is increased compared to the typical gibbsite, the key task herein is to identify and reveal how much the interlayer spacing has been increased. The position (2θ value) of the leftmost main peak of the XRD, which indicates the interlayer spacing, has been shifted to the left. This means an increase in the interlayer spacing. The height of the peak indicates how uniformly the interlayer spacing is formed by the pillar portions.

FIG. 5 is an XRD graph of typical gibbsite crystal structure disclosed in reference document 8, and FIG. 6 is an XRD graph of hydrotalcite, which is a layered-structure material, disclosed in reference document 9.

Referring to FIGS. 5, 6, 7A to 7E, and 8A to 8D, the patterns of the XRD graphs of FIGS. 7A to 7E and 8B are similar to that of the XRD graph of FIG. 5, but the position of the leftmost main peak thereof is shifted from 2θ=18.2° to 2θ=6.2°, which indicates that the gibbsite structure is maintained and the interlayer spacing has been increased from 4.86 Å to 14.1 Å. The patterns of the XRD graphs of FIGS. 7A to 7E and 8B are completely different from that of the hydrotalcite XRD graph of FIG. 6. In one or more embodiments, the peak corresponding to 14.1 Å disappears in FIG. 8A (Comparative Example 1), indicating that the amount of x is so small that the formation of the pillar structure fails. The pattern of the XRD graph of FIG. 8D is completely different from the patterns of the XRD graphs of FIGS. 5 and 6, and thus it can be seen that due to the high temperature of hydrothermal synthesis, a third structure that is neither gibbsite nor hydrotalcite is formed. From these results, it can be seen that the organic-inorganic hybrid compounds prepared according to Examples 1 to 5 and Comparative Example 2 are a compound that has, not the hydrotalcite structure, but the gibbsite structure with increased interlayer spacing, the organic-inorganic hybrid compounds prepared according to Comparative Example 1 (FIG. 8A) and Comparative Example 4 (FIG. 8D) are a compound that has, neither the hydrotalcite structure nor the gibbsite structure, but other structures (of no current interest), and in the case of the finally prepared material in Comparative Example 3 (FIG. 8C), since the pure gibbsite crystal structure was perfectly and strongly formed in the former process (S10) using the hydrothermal synthesis method, despite the implementation of the latter process (S20), terephthalate ions were not inserted, thereby synthesizing the pure gibbsite structure without increased interlayer spacing (FIG. 5).

Evaluation Example 3: Elemental Analysis of Organic-Inorganic Hybrid Compounds

Energy-dispersive X-ray spectroscopy (EDX) elemental analysis was performed on the organic-inorganic hybrid compounds prepared according to Examples 1 to 5 and Comparative Examples 1 and 2, and the results (elemental composition ratios of actually synthesized materials) are sequentially shown in Table 2. X-MaxN 50 of Horiba was used as the EDX device.

TABLE 2

| | Elemental composition (atom %) | | | | | Actual molar ratio (x) |
|---|---|---|---|---|---|---|
| | C | O | Al | Cl | Zn | Zn/Al |
| Example 1 | 14.85 | 63.38 | 20.38 | ~0 | 1.35 | 0.0662 |
| Example 2 | 12.46 | 63.79 | 22.41 | up to 0 | 1.33 | 0.0593 |
| Example 3 | 11.31 | 71.65 | 16.36 | ~0 | 0.67 | 0.041 |
| Example 4 | 11.37 | 71.3 | 16.74 | ~0 | 0.61 | 0.036 |
| Example 5 | 23.02 | 62.26 | 12.72 | ~0 | 1.9 | 0.149 |
| Comparative Example 1 | 10.38 | 71.22 | 17.98 | ~0 | 0.41 | 0.023 |
| Comparative Example 2 | 20.73 | 64.2 | 12.42 | ~0 | 2.49 | 0.200 |

Evaluation Example 4: Analysis of Real Image of Organic-Inorganic Hybrid Compounds The image of the organic-inorganic hybrid compound prepared according to Example 1 is shown in FIG. 9.

Figure 9:
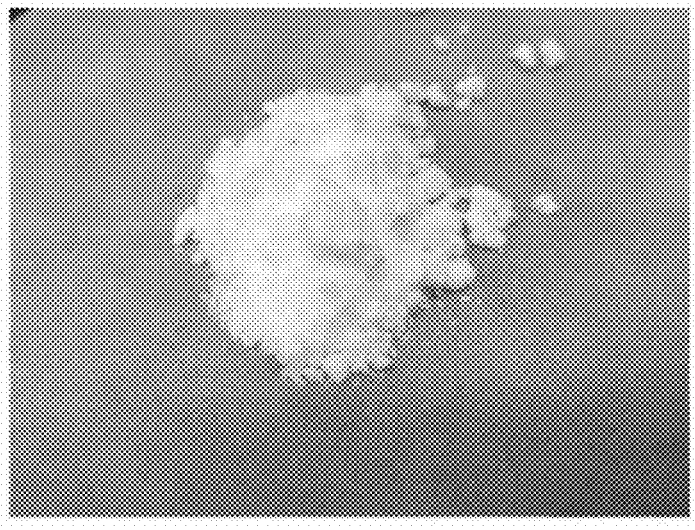
FIG. 9 shows an image of powder of an organic-inorganic hybrid compound prepared in Example 1 by a method other than a hydrothermal synthesis method, by using gibbsite prepared by a method other than a hydrothermal synthesis method.

Referring to FIG. 9, the sample prepared according to Example 1 is in the form of white powder. Although not shown, like FIG. 9, the images of the organic-inorganic hybrid compounds prepared according to Examples 2 to 5 show that the organic-inorganic hybrid compounds are all white powder.

The two intended structural conditions to be satisfied by the compound according to the present disclosure are as follows: the first, the pillar structure is firmly formed to support the increased interlayer spacing (the XRD peak at 14.1 Å position conspicuously appears), and the second, the pillar density is as low as possible (the x value is as small as possible) to secure as much empty space as possible between layers. Additional in-depth analysis of Examples 1 to 5 (especially, Examples 1 and 2) satisfying both conditions was conducted, and the analysis results are described in Evaluation Examples 5 to 7.

Figure 10A:
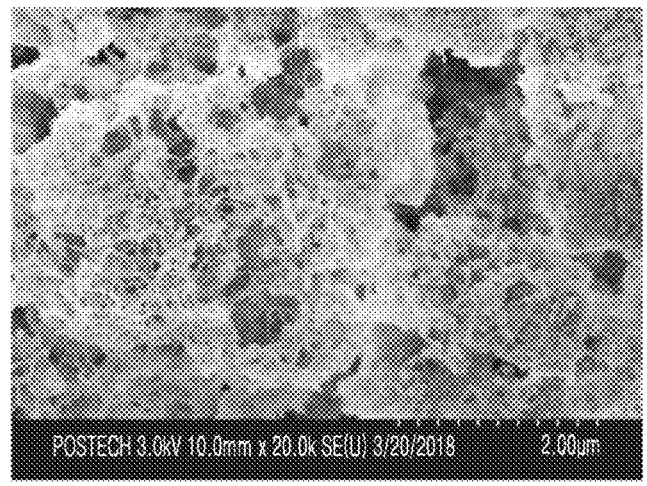
FIGS. 10A and 10B are scanning electron microscope (SEM) images of organic-inorganic hybrid compounds prepared in Examples 1 and 2 by a method other than a hydrothermal synthesis method, by using gibbsite prepared by a method other than a hydrothermal synthesis method.
Figure 10B:
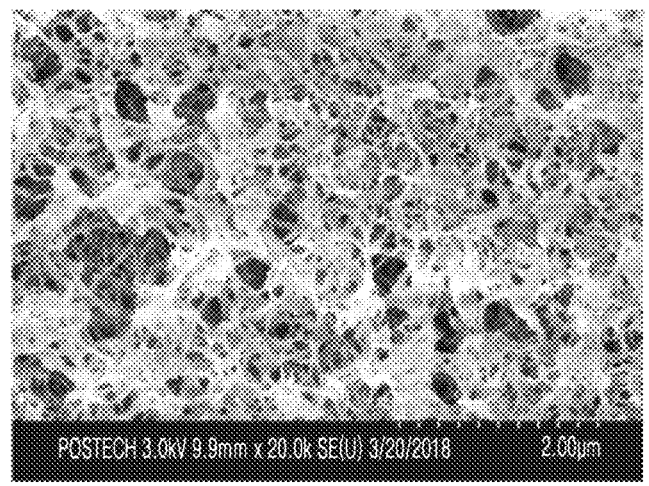

Evaluation Example 5: SEM Analysis of Surface Images of Organic-Inorganic Hybrid Compound The SEM images of the organic-inorganic hybrid compounds prepared according to Examples 1 and 2 are shown in FIGS. 10A and 10B, respectively. The SEM device used herein was JSM-6390LV from JEOL Inc.

Evaluation Example 6: Elemental Analysis of Organic-Inorganic Hybrid Compounds (XPS)

X-ray photoemission spectroscopy (XPS) elemental analysis was performed on the organic-inorganic hybrid compounds prepared according to Examples 1 and 2, and results thereof are shown in Table 3. MultiLab 2000 of THERMO VG SCIENTIFIC (U.K) was used as the XPS device.

TABLE 3

| | Elemental composition (atom %) | | | | | Actual molar ratio (x) |
|---|---|---|---|---|---|---|
| | C | O | Al | Cl | Zn | Zn/Al |
| Example 1 | 12.64 | 61.82 | 23.98 | ~0 | 1.56 | 0.0655 |
| Example 2 | 9.77 | 58.15 | 30.38 | -6 | 1.7 | 0.0560 |

Comparing the two elemental analysis methods (EDX and XPS) in Table 2 and Table 3, it can be seen that the molar ratios of Zn/Al are consistent with each other within the error range of the experiment (in the case of Example 1, 0.0662 versus 0.0655, and in the case of Example 2, 0.0593 versus 0.0560). In the present specification, the Zn/Al molar ratio of EDX in Table 2 was regarded as the actual value of x when needed for calculation.

Evaluation Example 7: Analysis of Brunauer-Emmett-Teller (BET) Characteristics of Gibbsite and Organic-Inorganic Hybrid Compounds The BET properties of the gibbsite prepared according to the former process (S10) of Example 1 and the organic-inorganic hybrid compounds prepared according to Examples 1 and 2 were analyzed, and the results are shown in Table 4 below.

TABLE 4

| | | BET surface area ($m^2/g$) | Pore volume ($cm^3/g$) |
|---|---|---|---|
| Gibbsite ($Al(OH)_3$) | Example 1 | 48.327 | 0.3126 |
| Organic-inorganic hybrid compound | Example 1 | 174.94 | 1.2487 |
| | Example 2 | 345.05 | 2.1353 |

Referring to Table 4, it can be seen that the organic-inorganic hybrid compounds prepared according to Examples 1 and 2 showed that both the BET surface area and the pore volume are significantly increased compared to the gibbsite prepared according to the former process (S10) of Example 1.

Evaluation Example 8: Structure Analysis of Organic-Inorganic Hybrid Compound (Identifying that Zn is Doped to the Octahedral Site of Gibbsite ($Al(OH)_3$))

There are six oxygen atoms around the octahedral site of gibbsite ($Al(OH)_3$). In detail, six oxygen atoms exist at positions corresponding to the six vertices of the octahedron of the gibbsite. This octahedral site corresponds to the central position of the octahedron of the gibbsite, and when a metal atom (for example, Zn) occupies this empty site, the metal atom forms coordinate bonds with all of the surrounding oxygen atoms, thereby completing a stable and strong bond structure having the coordination number of 6 (see reference document 10). In other words, as the metal atom occupies this empty space, the metal atom acts as an electron-pair acceptor, and the surrounding six oxygen atoms act as an electron-pair donor, forming strong coordinate bonds.

(Identification of Vertical Pillar Structure)

The most common and accurate method for measuring the single-layer thickness (d) of an organic-inorganic hybrid compound (see FIG. 1A) is to use an XRD graph.

The single-layer thickness (d=14.1 Å) of each of the organic-inorganic hybrid compounds prepared according to Examples 1 to 5 and Comparative Example 2 was obtained using the well known diffraction equation ($d=n\lambda/(2 \sin \theta)$) (reference document 11) wherein $n=1$, $\lambda=1.5406$ Å, which is the wavelength when the copper K$\alpha$ emission was used, and $\theta$=the value obtained from the experimentally measured angle ($2\theta$ value) that provides the leftmost highest peak in the XRD graphs of FIGS. 7A to 7E and FIGS. 8A to 8D.

Subsequently, regarding the organic-inorganic hybrid compounds prepared according to Examples 1 to 5 and Comparative Example 2, it was confirmed that the terephthalate ion had vertical pillar portions by comparing the single-layer thickness (d) with the length of the terephthalate ion. For example, in the case of the organic-inorganic hybrid compounds prepared according to Example 1, the thickness of the single layer of the original gibbsite ($Al(OH)_3$) is 4.86 Å and the length of the terephthalate ion is about 9.2 Å, and the sum thereof is consistent with the measured single-layer thickness (d) of 14.1 Å. Accordingly, it can be concluded that the terephthalate ion is vertically intercalated between two gibbsite ($Al(OH)_3$) layers.

However, the organic-inorganic hybrid compounds prepared according to Comparative Examples 1 and 3 and 4 were found to have no pillar structure.

(Calculation of Pillar Density and Average Distance Between the Pillar Portions)

By analyzing the structures of the organic-inorganic hybrid compounds prepared according to Examples 1 to 5 and Comparative Examples 1 to 4, the pillar density indicated by Equation 1 and the average distance between adjacent pillar portions were calculated. Results thereof are shown in Table 5 below. Here, actual Zn/Al molar ratio was used as x.

TABLE 5

| | pillar density (pillar/Å$^2$) | Average distance between the pillar portions (Å) |
|---|---|---|
| Example 1 | 1/167 | 13.7 |
| Example 2 | 1/186 | 14.7 |
| Example 3 | 1/269 | 17.6 |

TABLE 5-continued

| | pillar density (pillar/Å$^2$) | Average distance between the pillar portions (Å) |
|---|---|---|
| Example 4 | 1/306 | 18.8 |
| Example 5 | 1/74 | 9.2 |
| Comparative Example 1 | — | — |
| Comparative Example 2 | 1/55 | 8.0 |
| Comparative Example 3 | — | — |
| Comparative Example 4 | — | — |

Referring to Table 5, it can be seen that the organic-inorganic hybrid compounds prepared according to Examples 1 to 5 has a smaller pillar density and a longer average distance between adjacent pillar portions than the organic-inorganic hybrid compound prepared according to Comparative Example 2.

The organic-inorganic hybrid compounds prepared according to Comparative Examples 1, 3 and 4 did not have pillar structures. Thus, the pillar density and the average distance between adjacent pillar portions were not shown.

Evaluation Example 9: Analysis of Adsorption Characteristics of Activated Carbon and Organic-Inorganic Hybrid Compound The adsorption characteristics of activated carbon and the organic-inorganic hybrid compounds prepared according to Examples 1 to 5 and Comparative Example 2 were analyzed, and the results are shown in FIGS. 11, 12A to 12D, 13A, 13B, and 14 to 15.

Figure 11:
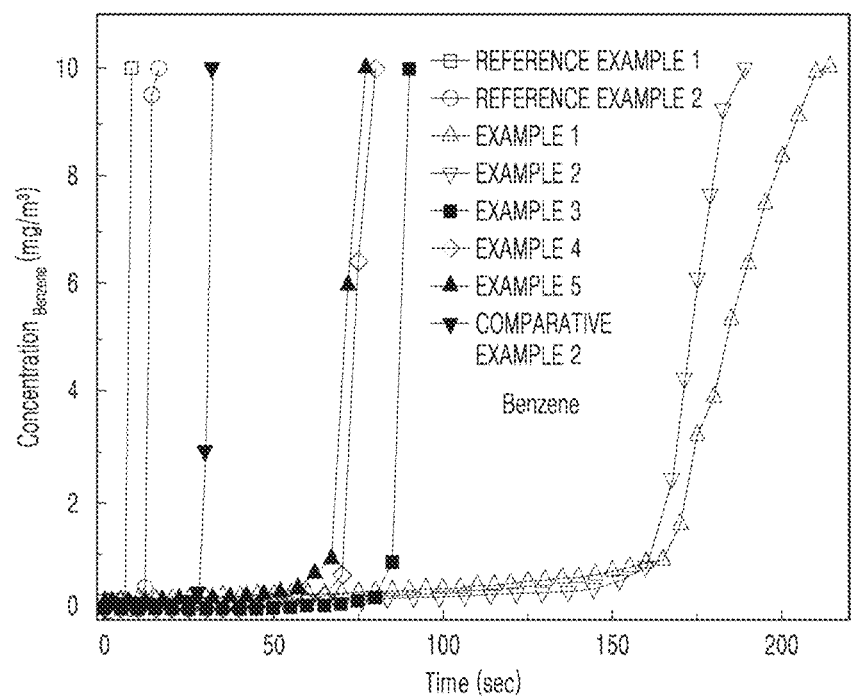
FIG. 11 is a graph showing the results of experiments of adsorption of benzene on activated carbon and the organic-inorganic hybrid compounds prepared according to Examples 1 to 5 and Comparative Example 2.
Figure 12A:
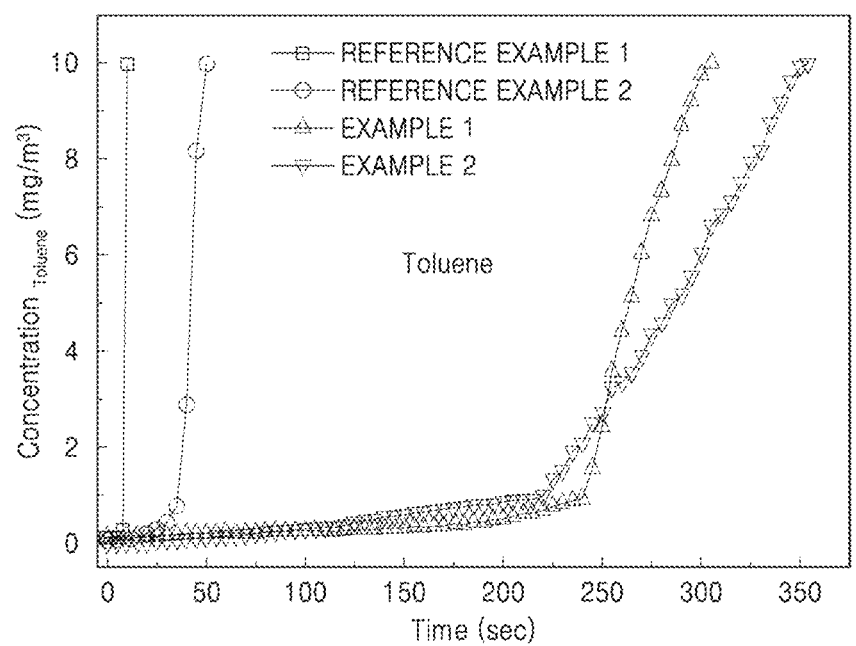
FIGS. 12A to 12D are graphs showing the results of experiments of adsorption of various volatile harmful materials on activated carbon and the organic-inorganic hybrid compounds prepared according to Examples 1 and 2.
Figure 12B:
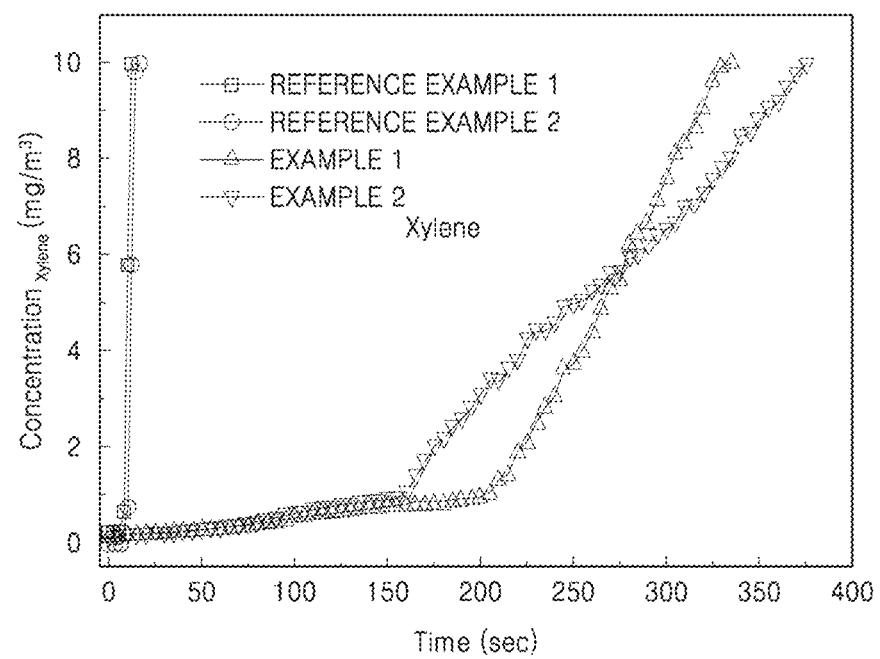
Figure 12C:
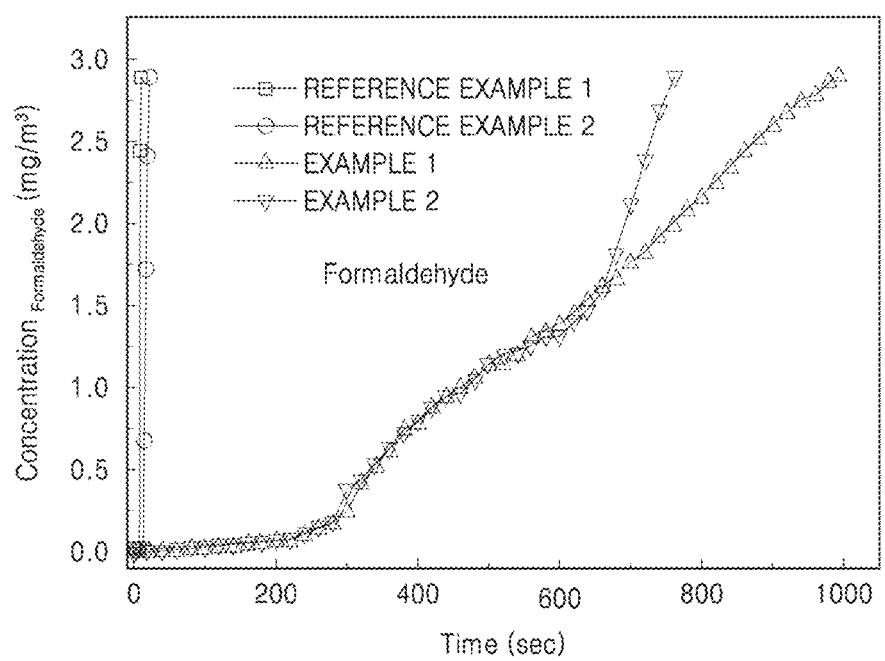
Figure 12D:
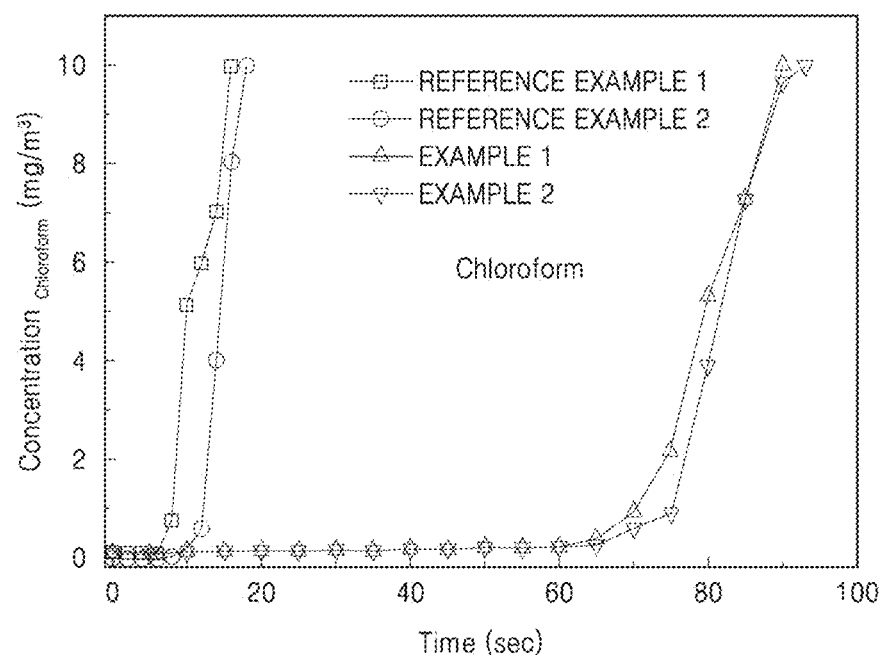

FIG. 11 is a graph showing the adsorption properties of benzene measured at a temperature of 25° C., FIG. 12A is a graph showing the adsorption properties of toluene measured at a temperature of 25° C., FIG. 12B is a graph showing the adsorption properties of xylene measured at a temperature of 35° C., FIG. 12C is a graph showing the adsorption properties of formaldehyde measured at a temperature of 50° C., and FIG. 12D is a graph showing the adsorption properties of chloroform measured at a temperature of 25° C. (all under atmospheric pressure, 1 atm).

In FIG. 11, the adsorption capabilities of the activated carbon and the organic-inorganic hybrid compounds prepared according to Examples 1 to 5 and Comparative Example 2, with respect to benzene, were compared and results thereof are shown. The capabilities of various adsorption materials to adsorb benzene (that continuously evaporates in the experimental device) and block the outflow thereof are shown as a function of time. Reference Example 1 (No sample) is the case in which there is no adsorption material, and Reference Example 2 (activated carbon) is the case in which activated carbon, which is widely used as a conventional adsorption material, is used. The value of 0 in the Y coordinate indicates that the outflow of a material is completely prevented. The measurement limit of the device for measuring the leaked harmful gas is 10.0 mg/m$^3$.

It can be seen that the sparsely pillared organic-inorganic hybrid compounds prepared according to Examples 1 to 5 (Example 1 and 2, in particular) were found to inhibit benzene from leaking to the outside by adsorbing benzene for a much longer time than activated carbon and the organic-inorganic hybrid compound prepared according to Comparative Example 2.

FIGS. 12A to 12D show the adsorption test results, similar to FIG. 11, of Examples 1 and 2 on toluene, xylene, formaldehyde, and chloroform, which are also representative volatile harmful materials. Here, the organic-inorganic hybrid compounds prepared according to Examples 1 and 2 were chosen for the test because these two showed outstanding adsorption abilities in FIG. 11. FIGS. 12A to 12D show superior adsorption abilities of the organic-inorganic hybrid compounds prepared according to Examples 1 and 2 compared to activated carbon.

Figure 13:
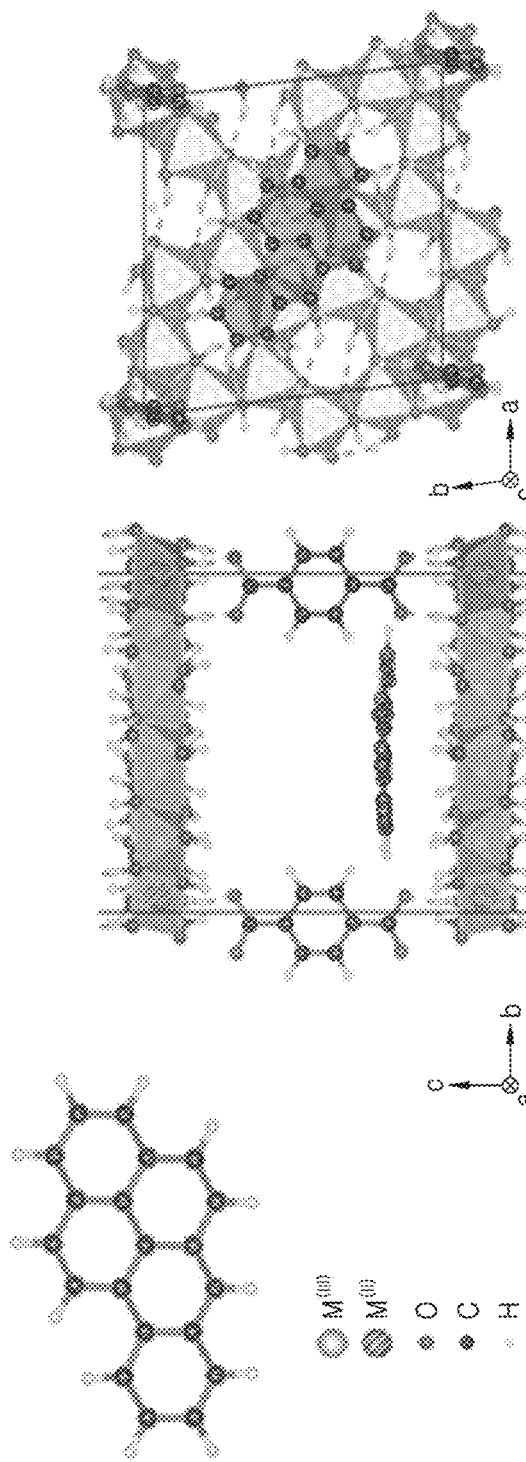
FIG. 13 is a schematic diagram showing the molecular structure of benzo(a)pyrene and the configuration of benzo(a)pyrene adsorbed on the organic-inorganic hybrid compound prepared according to Example 1.

FIG. 13 is a schematic diagram showing the molecular structure of benzo(a)pyrene, which is a representative polycyclic aromatic hydrocarbon and a carcinogen, and the configuration of benzo(a)pyrene adsorbed on the organic-inorganic hybrid compound prepared according to Example 1. Assuming x=0.0625, the pillar density is 1 pillar/(176.4 Å$^2$) and the average inter-pillar distance is about 14.3 Å. It can be seen that, since like benzene, toluene, and xylene, benzo(a)pyrene has flat-shape benzene rings and is large in size, and thus, only on the sparsely pillared organic-inorganic hybrid compound having a large inter-pillar distance as described in connection with FIG. 13, the entire molecular plane is completely adsorbed parallel to the plane of the compound. Since the entire large region of benzo(a)pyrene is adsorbed on the inner surface of the organic-inorganic hybrid compound, the magnitude of the adsorption energy is very high. Since benzo(a)pyrene is not volatile at room temperature, no such experimental data as shown in FIG. 12 are available. Instead, theoretical calculations (reference documents 1 and 2) through the computer simulation were performed, and the adsorption energy values thereof are shown in Table 7 below. For comprehensive understanding and verification, the adsorption energy to the organic-inorganic hybrid compound prepared according to Example 1 was calculated in the same way with respect to all the molecules of FIGS. 11, 12A to 12D, and results thereof are shown in Table 7 below (in the case of the organic-inorganic hybrid compound prepared according to Example 2, the inner surface has the same atomic structure as in the organic-inorganic hybrid compound prepared according to Example 1, and accordingly, the organic-inorganic hybrid compound prepared according to Example 2 has the same adsorption energy as the organic-inorganic hybrid compound prepared according to Example 1). For reference, the adsorption energy of $N_2$ and $O_2$ with respect to the organic-inorganic hybrid compound prepared according to Example 1 was also shown because these molecules are in competition with nitrogen ($N_2$) and oxygen ($O_2$) in air for adsorption. Since the magnitude of the adsorption energy of $N_2$ and $O_2$ is much smaller, it can be seen that when these harmful molecules are present in air, the adsorption thereof was dominant over air.

TABLE 7

| Harmful materials | Benzene | Toluene | Xylene | Formaldehyde | Chloroform | Benzo(a) pyrene | $N_2$ | $O_2$ |
|---|---|---|---|---|---|---|---|---|
| Adsorption energy (kJ/mol) | −48 | −54 | −64 | −49 | −54 | −114 | −17 | −15 |

Evaluation Example 10: Calculation of Adsorption Energy of Harmful Materials to Organic-Inorganic Hybrid Compound Among the harmful materials, especially the adsorption energy of vehicles' exhaust gases and greenhouse gases (NO, $NO_2$, $N_2O$, $SO_2$, CO, $CO_2$, $CH_4$), associated with the atmospheric environment, on the organic-inorganic hybrid compound prepared according to Example 1 was calculated using the method of reference documents 1 and 2, and results thereof are shown in Table 8. Additionally, the adsorption energy of chlorine gas ($Cl_2$) and phenol ($C_6H_6O$), which are toxic chemicals, hydrogen cyanide, (HCN), acrolein ($C_3H_4O$), and nicotine ($C_{10}N_2H_{14}$), which are related to cigarette smoking and are toxic to the human body, on the organic-inorganic hybrid compound prepared according to Example 1, was calculated, and results thereof are shown in Table 9. These molecules may be adsorbed on the adsorbent surface by the weak van der Waals interactions that are common to all atoms, but in the case of sparsely pillared organic-inorganic hybrid compounds, there are strong electric and electric field gradient therein, so electric dipoles and electric quadrupoles make a large contribution to the adsorption. For molecules of which dipoles are intrinsically nonzero, the dipole (p) has the largest contribution to the adsorption and the dipole induced by the polarizability (a) and the electric quadrupole (Q) make additional contributions to the adsorption. For molecules of which dipoles are zero, the dipole induced by the polarizability (a) and the electric quadrupole (Q) make contributions to the adsorption. In the case of methane ($CH_4$), the dipole and the quadrupole are both zero, but since H atoms in methane directly interact with the organic-inorganic hybrid compound, a similar adsorption energy value may be obtained.

Figure 14:
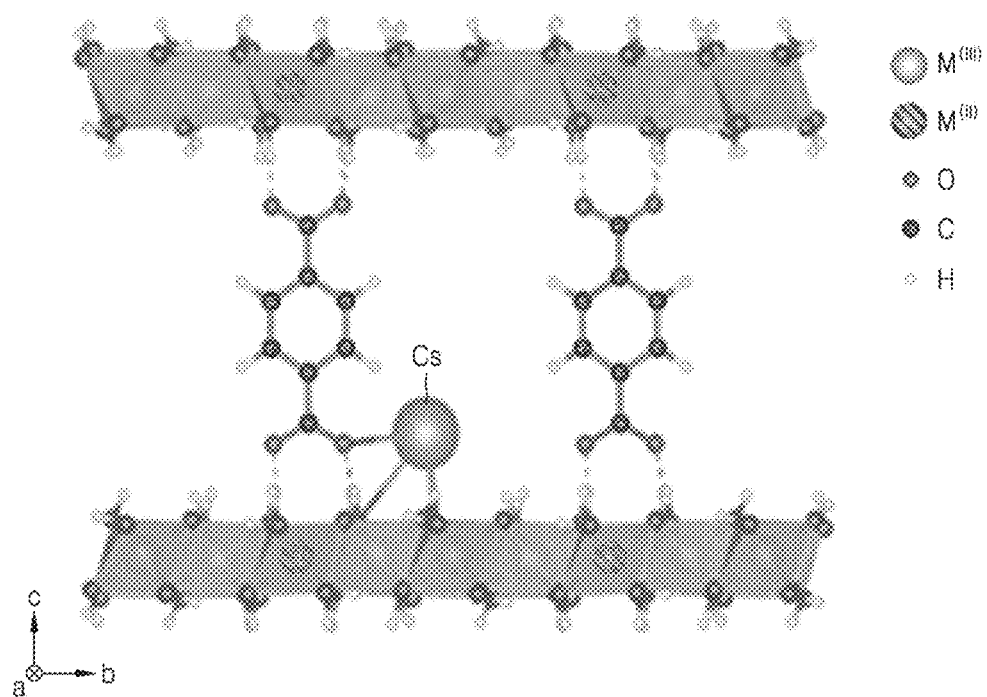
FIG. 14 is a schematic diagram of cesium (Cs) adsorbed on the organic-inorganic hybrid compound prepared according to Example 1.
Figure 15:
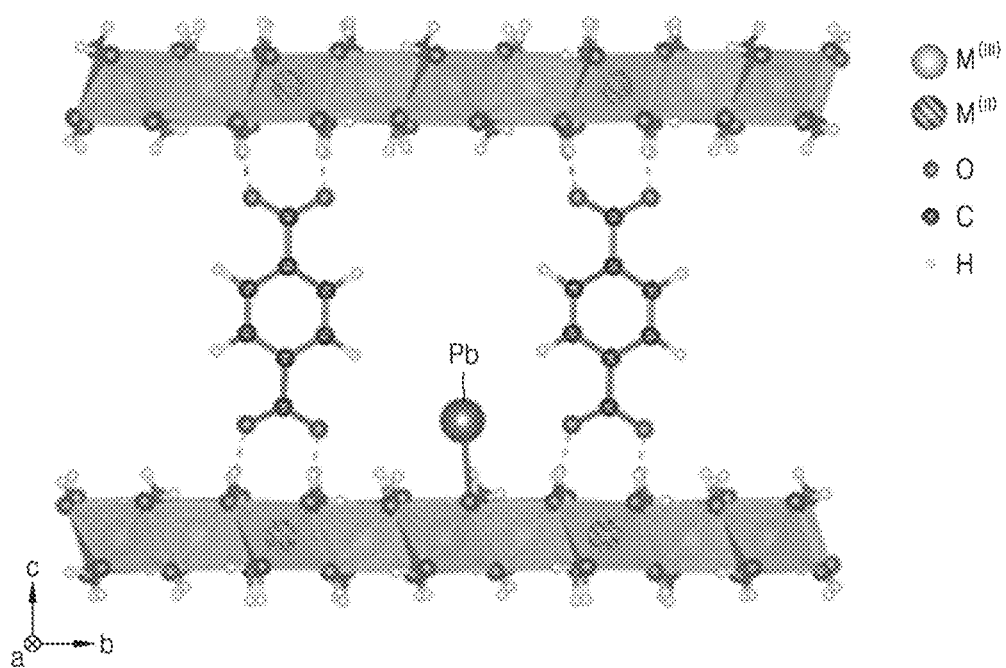
FIG. 15 is a schematic diagram of lead (Pb) adsorbed on the organic-inorganic hybrid compound prepared according to Example 1.

Meanwhile, the organic-inorganic hybrid compound has also the ability to adsorb radioactive materials and harmful heavy metals. FIG. 14 is a schematic diagram of cesium (Cs) adsorbed on the organic-inorganic hybrid compound prepared according to Example 1. FIG. 15 is a schematic diagram of lead (Pb) adsorbed on the organic-inorganic hybrid compound prepared according to Example 1.

In particular, cesium (Cs), which is a representative radioactive material, and lead (Pb), which is a representative harmful heavy metal, are usually found as being dissolved in water, thereby contaminating the water. The adsorption energy of Cs and Pb on the sparsely pillared organic-inorganic hybrid compound, as shown in Table 8, are −230 kJ/mol and −91 kJ/mol, respectively. That is, it can be seen that Cs and Pb are so strongly adsorbed thereon and thus collected to the sparsely pillared organic-inorganic hybrid compound that the desortion thereof does not happen. This is due to the extremely strong polarizability of Cs (59.6× $10^{-24}$ $cm^3$) and the relatively strong polarizability of Pd ($6.8×10^{-24}$ $cm^3$). In particular, Cs forms a strong ionic bond with the organic-inorganic hybrid compound prepared according to Example 1. As a comparative example, the adsorption energy of water ($H_2O$) is −59 kJ/mol. Accordingly, it can be seen that when dissolved in water, these radioactive materials and harmful heavy metals are adsorbed much more strongly than water molecules.

Chlorine gas and phenol, which may be discharged from a water purification process or chemical process, are also notable harmful materials to which human can be exposed in daily life, and can be adsorbed on the sparsely organic-inorganic hybrid compound with adsorption energy as shown in Table 9. In the case of toxic materials associated with smoking (primary, secondary, or tertiary smoking) (reference document 12), the amount of materials that have passed through a filter can be selectively controlled by adding the sparsely pillared organic-inorganic hybrid compound to the filter and adsorbing the materials on the added sparsely pillared organic-inorganic hybrid compound.

Regarding these materials, absorption energy calculation results and the absolute values of the dipole (p), polarizability (a), and quadrupole (0) disclosed in reference documents 4 and 5 are shown in Tables 8 and 9. Here, the dipole unit is Debye (D) (1D=3.336×$10^{-30}$ C·m), the polarizability unit is $10^{-24}$ $cm^3$, and the quadrupole unit is $10^{-26}$ esu·$cm^2$. The contribution thereof to the adsorption energy varies depending on molecules, and due to being mixed with hydrogen bond energy, van der Waals energy, etc., it is impossible to separate each contribution. However, approximately, the total contribution thereof (that is, the dipole and quadrupole energy) is estimated as −10 kJ/mol to −20 kJ/mol.

TABLE 8

|  | NO | $NO_2$ | $N_2O$ | $SO_2$ | CO | $CO_2$ | $CH_4$ | Cs | Pb |
|---|---|---|---|---|---|---|---|---|---|
| Adsorption energy (kJ/mol) | −35 | −27 | −28 | −50 | −29 | −31 | −32 | −230 | −91 |
| p | 0.16 | 0.32 | 0.16 | 1.63 | 0.11 | 0 | 0 | 0 | 0 |
| α | 1.7 | 3.0 | 3.0 | 4.0 | 1.95 | 2.91 | 2.59 | 59.6 | 6.8 |
| \|Q\| | 1.8 | 4 | 3.0 | 4.4 | 2.5 | 4.3 | 0 | 0 | 0 |

TABLE 9

|  | $Cl_2$ | Phenol | HCN | Acrolein | Nicotine |
|---|---|---|---|---|---|
| Adsorption energy (kJ/mol) | −78 | −38 | −57 | −57 | −103 |
| p | 0 | 1.22 | 2.99 | 3.12 | 1 |
| α | 4.61 | 11.1 | 2.5 | 6.38 | 16 |
| \|Q\| | 6.14 | 4 | 4.4 | 2 | 7 |

Evaluation Example 11: Analysis of Hydrogen Storage Ability of Organic-Inorganic Hybrid Compounds As described above, the sparsely pillared organic-inorganic hybrid compound has a higher $H_2$ storage ability than existing hydrogen molecule adsorption materials due to the contribution of internal electric fields and electric field gradient.

Figure 16:
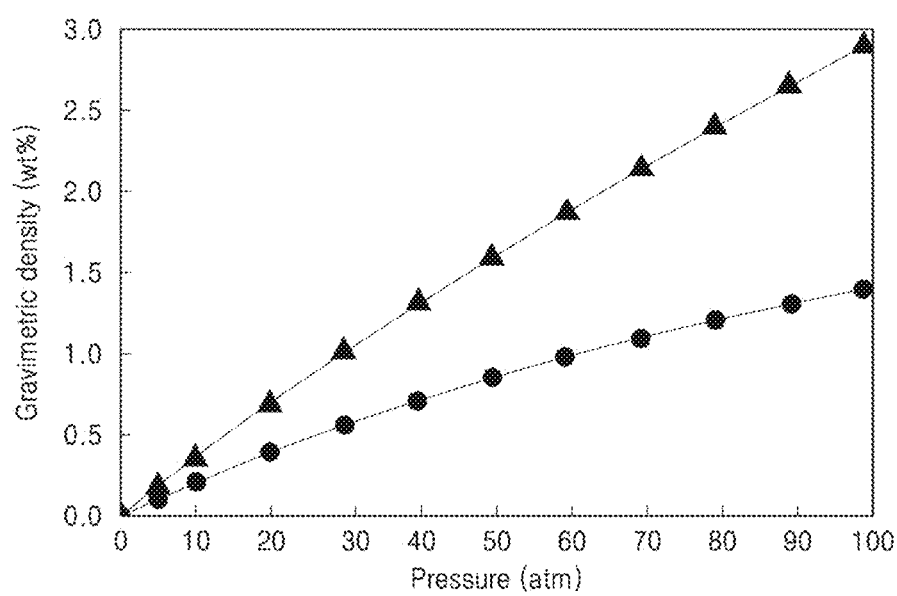
FIG. 16 is a graph showing the amount of hydrogen stored in the organic-inorganic hybrid compound prepared according to Example 1.

The hydrogen storage capacity at 25° C. was obtained by using the representative computational method called the Grand Canonical Monte Carlo (GCMC) method widely employed for the gas storage calculation (reference document 13). The adsorption energy required as input data for the GCMC calculation was obtained by using the same method as previously performed with harmful materials (reference documents 1 and 2), and the additionally required interaction energy between two hydrogen molecules was calculated by using the method of reference document 14. The result of the GCMC calculation at a temperature of 25° C. as a function of pressure is presented as the line constituted of circle dots in FIG. 16. During the GCMC calculation, the contribution of the meso- and macro-pores existing in real materials is not included. Accordingly, when the contribution of the meso- and macro-pore volume (up to 2.1 $cm^3$/g) to the storage is added up, about 3% by weight of hydrogen (about 30 g of hydrogen per 1 kg of storage material) at 25° C. and 100 atm is stored in total (the line constituted of triangular dots in FIG. 16). Since the energy contained in 30 g of hydrogen is about 1,000 Wh (watt·hour), it can be said that 1,000 Wh is stored per 1 kg of the organic-inorganic hybrid compound prepared according to Example 1. Assuming that the efficiency of a hydrogen fuel cell used in a hydrogen vehicle is about 50%, 500 Wh/kg may be stored, which is about 2.5 times a representative value (about 200 Wh/kg) of a lithium ion battery used in an electric vehicle. In terms of volume, 14 g/L of hydrogen (about 14 g of hydrogen per 1 L of storage material) is stored, which is 1.8 times greater than the amount stored in the hydrogen tank (7.7 g/L) at the same conditions of 25° C. and 100 atm. For reference, the explanation about adding the contribution of the pore volume (that is, adding the contribution of the pore volume to the excess storage measured in the experiment) to calculate the total hydrogen storage is disclosed in reference document 15. Through the above analysis, it can be seen that the organic-inorganic hybrid compound is a potent hydrogen molecule storage material.

In this application, Examples 1 to 5 and Comparative Example 2 illustrate only a combination of Al as a trivalent metal, Zn as a divalent metal, and terephthalic acid as a dicarboxylic acid, but those of ordinary skill in the art may easily conduct other combinations of trivalent metal, divalent metal, and dicarboxylic acid according to the same method as described in Examples 1 to 5 and Comparative Example 2, and it would easily expect that the obtained results would be similar to that obtained using the combination of Al, Zn, and terephthalic acid.

An organic-inorganic hybrid compound according to an embodiment of the present disclosure has the following advantages.

(1) The pillar density is very low and the structural stability is still excellent.

(2) The pore volume and the surface area are increased because a lot of empty spaces are formed between inorganic material layers.

(3) Because the pillar density is remarkably low, much less amount of metal (for example, Zn) doped to the octahedral site of an inorganic material layer having a gibbsite structure and much less amount of an organic material acting as a pillar (for example, terephthalate ion) are required.

(4) Distances among pillar portions are long (for example, when the nominal value of x in Formula 1 is 0.0625, the average inter-pillar distance is beyond 14 Å, and thus, relatively large molecules (for example, benzo(a)pyrene known as a carcinogen) may well be intercalated into between pillar portions and adsorbed therein.

(5) Compared with other materials having the same volume, the amount of constituent substances is smaller, leading to a decrease in weight. The intrinsic density of this material is, in the case of pure gibbsite without the pillar structure, 2.42 $g/cm^3$. However, when $M^{(II)}=Zn^{2+}$, $M^{(III)}=Al^{3+}$, $A^{2-}$=terephthalate ion, and x=0.0625, the density is decreased to 0.99 $g/cm^3$. When A is terephthalic acid, the density of the compound having the pillar structure can be (0.833+2.45x) $g/cm^3$, when expressed as the function of x.

(6) Due to the increase in empty spaces, not only does the amount of adsorbed material is increased, but also the movement of molecules within the empty space becomes much easier and faster, so the required time for all desired molecular reactions (adsorption, storage, reaching equilibrium, etc.) is greatly reduced.

(7) Compared to the case of other porous materials such as zeolite and metal-organic framework (including covalent organic framework), hydro- or solvo-thermal synthesis, etc., which are energy-consuming process, are not needed in the synthesis of the organic-inorganic hybrid compounds according to the present disclosure, and the industrial mass-production can be made at an affordable price.

(8) Carbon nanotubes and graphene oxide have also been studied in recent years for the purpose of adsorption or storage, but even compared with them, the organic-inorganic hybrid compounds according to the present disclosure are significantly advantageous in terms of performance based on price and mass production potential.

(9) Compared to all other prior arts, the organic-inorganic hybrid compounds according to the present disclosure can be manufactured under the conditions of low energy and low pressure so that low manufacturing costs and improved occupational safety can be secured.

(10) No extra surfactants or catalysts are required in the manufacturing process.

(11) From among constituent substances, Al and Zn, which are the most representative metals used in the present disclosure, do not belong to harmful heavy metals (Cd, Hg, Pb, etc.). Also, terephthalic acid is an inexpensive and harmless organic material that is already used extensively for industrial use worldwide. In particular, Zn, the representative metal used for the doping for pillar formation, is also inexpensive among metals. For comparison, the source materials used for lithium ion batteries, such as Li, Co, and Ni, are already expensive and the price thereof is continuously rising as the demand is expected to increase in the future. It is possible to implement the present disclosure without using these expensive materials at all.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

LIST OF REFERENCE DOCUMENTS reference document 1. Perdew, J. P.; Burke, K,; Emzerhof, M., Phys. Rev. Lett. 1996, 77, 3865-3868
reference document 2. Grimme, S., J. Comput. Chem. 2006, 27(15), 1787-1799
reference document 3. N. L. Rosi et al., Science 2003, 300, 1127-1129
reference document 4. Lide (ed.), CRC Handbook of Chemistry and Physics, 75th ed., 1994, pp 9-44 and 10-196
reference document 5. D. E. Stogryn et al., Mol. Phys. 11, 371(1996)
reference document 6. J. D. Jackson, Classical Electrodynamics, 2nd ed. John Wiley and Sons, New York 1975, pp 142, 161, and 165.
reference document 7. C. Kittel and H. Kroemer, Thermal Physics, 2nd ed. Freeman and Company, San Francisco 1980, p 265.
reference document 8. T. R. Reddy, K. Thyagarajan, O. A. Montero, S. R. L. Reddy, T. Endo, Journal of Minerals and Materials Characterization and Engineering, 2014, 2, pp 114-120.

reference document 9. A. OBADIAH, R. KANNAN, P. RAVICHANDRAN, A. RAMASUBBU, S. VASANTH KUMAR, Digest Journal of Nanomaterials and Biostructures, Vol. 7, No. 1, January-March 2012, p 321-327 reference document 10. J. E. McMurry and R. C. Fay, General Chemistry, Pearson 2014, Chap. 20.5 (Translation) "General Chemistry" Freedom Academy 2014, p 838.

reference document 11. N. W. Ashcroft and N. D. Mermin, Solid State Physics, Thomson Learning, Singapore 1976, p 96 reference document 12. https://en.wikipedia.org/wiki/Tar_(tobacco_residue)

reference document 13. B. K. Peterson & K. E. Gubbins, Molec. Phys. 1987, 62, 215-226 reference document 14. Silvera, I. F. & Goldman, V. V. J. Chem. Phys. 1978, 68, 4209-4213 reference document 15. M. P. Suh et al., Chemical Reviews 2012, 112, 782-835

What is claimed is:

1. A method of preparing an organic-inorganic hybrid compound, the method comprising:
preparing a compound having a gibbsite structure by a method other than a hydrothermal synthesis method, using a trivalent metal cation source, an alkali imparting agent, and a first solvent (S10); and
preparing an organic-inorganic hybrid compound by a method other than a hydrothermal synthesis method, using the compound having the gibbsite structure, a divalent metal cation source, dicarboxylic acid, and a second solvent (S20),
wherein the organic-inorganic hybrid compound is represented by Formula 1

  [Formula 1]

where $M^{(II)}$ is a divalent metal cation, $M^{(III)}$ is a trivalent metal cation, $A^{2-}$ is a dicarboxylate ion, and x satisfies the condition of $0<x<0.2$.

2. The method of claim 1, wherein the trivalent metal cation source is a source of a trivalent metal cation including $Al^{3+}$, $Fe^{3+}$, $Cr^{3+}$, $B^{3+}$, $Ga^{3+}$, $In^{3+}$, $Y^{3+}$, or a combination thereof.

3. The method of claim 1, wherein the alkali imparting agent comprises NaOH, LiOH, KOH, $LiBH_4$, $NaBH_4$, $KBH_4$, LiH, NaH, $LiAlH_4$, $NaAlH_4$, $KAlH_4$, $(i-Bu_2AlH)_2$, $LiHCO_3$, $NaHCO_3$, $KHCO_3$, $Li_2MO$, $Na_2CO_3$, $K_2COM$, $NH_4OH$, or a combination thereof.

4. The method of claim 1, wherein the first solvent or the second solvent comprises water.

5. The method of claim 1, wherein the compound having the gibbsite structure is amorphous as identified from X-ray diffraction (XRD) analysis results.

6. The method of claim 1, wherein the divalent metal cation source is a source of a divalent metal cation including $Zn^{2+}$, $Mn^{2+}$, $Co^{2+}$, $Ni^{2+}$, $Cu^{2+}$, $Mg^{2+}$, $Ca^{2+}$, $Sr^{2+}$, $Ba^{2+}$, or a combination thereof.

7. The method of claim 1, wherein the dicarboxylic acid comprises terephthalic acid, oxalic acid, malonic acid, succinic acid, glutaric acid, 2-methylglutaric acid, 3-methylglutaric acid, adipic acid, pimelic acid, suberic acid, azelaic acid, sebacic acid, undecanedioic acid, dodecanedioic acid, brassylic acid, tetradecanedioic acid, fumaric acid, 2,2-dimethylglutaric acid, maleic acid, acetylenedicarboxylic acid, glutaconic acid, 2-disendioic acid, traumatic acid, muconic acid, glutinic acid, citraconic acid, mesaconic acid, itaconic acid, tartronic acid, mesosalic acid, malic acid, tartaric acid, oxalacetic acid, aspartic acid, glutamic acid, diaminopimelic acid, saccharic acid, 2,6-naphthalenedicarboxylic acid, or combination thereof.

8. The method of claim 1, wherein the process (S10) comprises preparing a first metal salt solution by dissolving the trivalent metal cation source in the first solvent (S10-1), preparing an alkali solution by dissolving the alkali imparting agent in the first solvent (S10-2), and synthesizing the compound of the gibbsite structure by mixing the first metal salt solution and the alkali solution at room temperature (S10-3).

9. The method of claim 1, wherein the process (S20) comprises preparing a mixture by mixing the compound of the gibbsite structure, the divalent metal cation source, the dicarboxylic acid, and the second solvent (S20-1), and synthesizing an organic-inorganic hybrid compound by heating the mixture at a temperature of about 50° C. to about 90° C. and maintaining the temperature for about 3 hours to about 72 hours (S20-2).

* * * * *